United States Patent
Bruemmer Prestley et al.

(10) Patent No.: US 6,676,648 B2
(45) Date of Patent: Jan. 13, 2004

(54) ABSORBENT GARMENT HAVING ASYMMETRIC LONGITUDINAL ABSORBENT PAD

(75) Inventors: Mary Anne Bruemmer Prestley, Appleton, WI (US); Marianne Keevill Leick, Appleton, WI (US); Gregory James Hess, Fremont, WI (US); David Arthur Fell, Neenah, WI (US); Sarah Jane Marie Freiburger, Kaukauna, WI (US); Amy Lynn Fletcher, Appleton, WI (US); Cornelis Jacobus Bosselaar, Appleton, WI (US); Joseph Patrick Fell, Appleton, WI (US); Jacqueline Ann Gross, Neenah, WI (US); John Anthony Rooyakkers, Little Chute, WI (US); Kenneth Raymond Schueler, Jr., Appleton, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 324 days.

(21) Appl. No.: 09/796,966

(22) Filed: Mar. 1, 2001

(65) Prior Publication Data
US 2001/0031957 A1 Oct. 18, 2001

Related U.S. Application Data

(63) Continuation-in-part of application No. 09/185,894, filed on Nov. 4, 1998, now abandoned.

(51) Int. Cl.[7] ............................................. A61F 13/15

(52) U.S. Cl. ..................... 604/385.23; 604/385.24; 604/385.01; 604/385.101; 604/385.25; 604/385.29; 604/385.3

(58) Field of Search ................ 604/385.24, 385.23, 604/385.01, 385.101, 385.25, 385.29, 385.3

(56) References Cited

U.S. PATENT DOCUMENTS

| | | | |
|---|---|---|---|
| 3,338,992 A | 8/1967 | Kinney | 264/24 |
| 3,341,394 A | 9/1967 | Kinney | 161/72 |
| 3,502,763 A | 3/1970 | Hartmann | 264/210 |
| 3,542,615 A | 11/1970 | Dobo et al. | 156/181 |
| 3,692,618 A | 9/1972 | Dorschner et al. | 161/72 |
| 3,802,817 A | 4/1974 | Matsuki et al. | 425/66 |
| 4,041,203 A | 8/1977 | Brock et al. | 428/157 |
| 4,100,324 A | 7/1978 | Anderson et al. | 428/288 |
| 4,315,508 A | 2/1982 | Bolick | 128/289 |
| 4,340,563 A | 7/1982 | Appel et al. | 264/518 |

(List continued on next page.)

FOREIGN PATENT DOCUMENTS

| | | | |
|---|---|---|---|
| EP | 0269401 | 6/1988 | A41B/13/02 |
| EP | 0345664 | 12/1989 | A61F/13/16 |
| EP | 0539703 | 5/1993 | A61F/13/15 |
| EP | 0 627 210 A2 | 5/1994 | A61F/13/15 |
| EP | 0627210 | 12/1994 | A61F/13/15 |
| EP | 0 763 353 A2 | 3/1997 | A61F/13/15 |
| EP | 0763353 | 3/1997 | A61F/13/15 |
| WO | WO 95/14453 | 6/1995 | A61F/13/15 |
| WO | 9522951 | 8/1995 | A61F/13/15 |
| WO | 9706763 | 2/1997 | A61F/13/15 |
| WO | 9829080 | 7/1998 | A61F/13/56 |
| WO | WO 00/02510 | 1/2000 | A61F/13/15 |

Primary Examiner—John J. Calvert
Assistant Examiner—Angela J Grayson
(74) Attorney, Agent, or Firm—Thomas J. Connelly; Douglas G. Glantz

(57) ABSTRACT

A disposable absorbent garment has a front region, a back region, and a central region, each region having a length along a longitudinal axis of one third of the length of the absorbent garment. An absorbent pad positioned within the regions has a length of absorbent pad in the back region divided by a length of absorbent pad in the front region and central region less than 0.10, and the length in the front region is greater than the length in the back region.

27 Claims, 7 Drawing Sheets

U.S. PATENT DOCUMENTS

| | | | |
|---|---|---|---|
| 4,381,782 A | 5/1983 | Mazurak et al. | 604/368 |
| 4,610,681 A | 9/1986 | Strohbeen et al. | 604/396 |
| 4,641,381 A | 2/1987 | Heran et al. | 2/400 |
| 4,646,362 A | 3/1987 | Heran et al. | 2/400 |
| 4,652,487 A | 3/1987 | Morman | 428/138 |
| 4,655,760 A | 4/1987 | Morman et al. | 604/385 A |
| 4,657,802 A | 4/1987 | Morman | 428/152 |
| 4,668,230 A | 5/1987 | Damico et al. | 604/385 A |
| 4,699,823 A | 10/1987 | Kellenberger et al. | 428/219 |
| 4,720,415 A | 1/1988 | Vander Wielen et al. | 428/152 |
| 4,731,070 A | 3/1988 | Koci | 604/385 R |
| 4,781,966 A | 11/1988 | Taylor | 428/152 |
| 4,789,699 A | 12/1988 | Kieffer et al. | 524/271 |
| 4,798,603 A | 1/1989 | Meyer et al. | 604/378 |
| 4,818,464 A | 4/1989 | Lau | 264/510 |
| 4,826,499 A | 5/1989 | Ahr | 604/389 |
| 4,886,512 A | 12/1989 | Damico et al. | 609/385.2 |
| 4,904,249 A | 2/1990 | Miller et al. | 604/378 |
| 5,145,727 A | 9/1992 | Potts et al. | 428/198 |
| 5,147,343 A | 9/1992 | Kellenberger | 604/368 |
| 5,169,706 A | 12/1992 | Collier, IV et al. | 428/152 |
| 5,178,931 A | 1/1993 | Perkins et al. | 428/198 |
| 5,188,885 A | 2/1993 | Timmons et al. | 428/198 |
| 5,192,606 A | 3/1993 | Proxmire et al. | 428/284 |
| 5,364,382 A | 11/1994 | Latimer et al. | 604/378 |
| 5,429,629 A | 7/1995 | Latimer et al. | 604/378 |
| 5,486,166 A | 1/1996 | Bishop et al. | 604/366 |
| 5,490,846 A | 2/1996 | Ellis et al. | 604/366 |
| 5,509,915 A | 4/1996 | Hanson et al. | 604/378 |
| 5,551,093 A | 9/1996 | Stricker | 2/406 |
| 5,554,145 A | 9/1996 | Roe et al. | 604/385.2 |
| 5,651,862 A | 7/1997 | Anderson et al. | 162/127 |
| 5,769,835 A | 6/1998 | Fell et al. | 604/385.2 |
| 5,810,797 A | 9/1998 | Menard et al. | 604/378 |
| 5,858,013 A | 1/1999 | Kling | 604/386 |
| 6,083,210 A | 7/2000 | Young et al. | 604/367 |

…

ABSORBENT GARMENT HAVING ASYMMETRIC LONGITUDINAL ABSORBENT PAD

This patent application is a Continuation-in-part of prior, U.S. Patent Application Serial No. 09/185,894, filed Nov. 4, 1998 now abandoned.

BACKGROUND OF THE INVENTION

1. Technical Field

This invention relates to an absorbent garment. In one aspect, this invention relates to diapers, pull-on pants, briefs, and absorbent undergarments. In one aspect, this invention relates to an absorbent undergarment having an absorbent pad shifted forward for containing and absorbing human body waste.

2. Background

Absorbent garments for absorbing human body waste discharges include baby diapers, feminine care products, and incontinence garments. Absorbent garments require an aqueous-liquid-pervious body-side liner, an absorbent pad containing one or more layers for receiving and absorbing a human body waste discharge, and an aqueous-liquid-impervious backing member for containing the human body waste discharge.

INTRODUCTION TO THE INVENTION

Some absorbent garments perform satisfactorily for their intended purpose, but there remains a need to provide an undergarment having preferred absorption characteristics, preferred utilization of the absorbent material, and preferred waste containment characteristics, preferably with a minimum of discomfort to the wearer and a more discrete appearance. Undergarments have not served to facilitate the transfer of aqueous liquids to an entire area of an absorbent layer or layers, including the distal ends of the absorbent layer or layers. Waste absorption is concentrated in a small region of the absorbent layer which results in an under-utilization of much of the absorbent capacity of the undergarment.

Absorbent undergarments and other absorbent personal care garment-like products are worn in a "J" configuration. In a "J" configuration, the front region of the undergarment is worn lower on the wearer's body than the back region of the undergarment. The center of the undergarment does not coincide with the point of insult. Rather, the point of insult occurs toward the front region of the undergarment. Accordingly, currently available undergarments do not provide adequate absorbent material at the point of insult.

Absorbent undergarments having absorbent pads including centrally located acquisition zones do not provide a preferred absorbency, resulting in product failure.

Some undergarments for absorbing and containing human body waste discharge have been bulky and somewhat ineffective. The absorbent pad has an absorbent capacity location not fully utilized in a bulky configuration, particularly in the central portion and the back region. Such undergarments are uncomfortable to wear, especially if the wearer is an active adult. Such undergarments are costly and inefficient in placement of the absorbent material in the back region where it is not used, but rather the absorbent material in the back region is wasted.

A need exists for an absorbent undergarment having preferred absorbent characteristics and preferred containment characteristics while still being comfortable to wear.

SUMMARY OF THE INVENTION

The article and method of the present invention provide a disposable absorbent garment having an initial expanded shape, a longitudinal axis and a transverse axis, a front region, and a back region. The front region and the back region are positioned oppositely on the longitudinal axis, and a central region is positioned between the front region and the back region. The front region, the back region, and the central region each have a length along the longitudinal axis of one third of the length of the absorbent garment. The article and method of the present invention provide an aqueous-liquid-impervious backing member, an aqueous-liquid-pervious body-side liner joined to the backing member to form a joined body-side liner and backing member connected along a periphery of the joined body-side liner and backing member, a rectangular absorbent pad having a front end edge and a back end edge positioned between the body-side liner and the backing member inboard of the periphery of the joined liner and the backing member, and elastic gathers aligned along longitudinally extending margins of the periphery, rendering the garment elastically contractible and body-conforming in the region adjacent the crotch of the wearer. The article and method of the present invention provide the absorbent pad positioned within the regions such that the length of the absorbent pad in the back region divided by the length of the absorbent pad in the front region and the central region is less than 0.10 and the length of the absorbent pad in the front region is greater than the length of absorbent pad in the back region.

DETAILED DESCRIPTION

The present invention provides an absorbent undergarment having preferred absorption, containment, and comfort. The undergarment of the present invention provides an absorbent pad positioned in the front region and the central region such that the absorbent pad is placed asymmetrically in the longitudinal dimension of the garment. The asymmetrical placement of the absorbent pad in the longitudinal dimension of the garment facilitates the formation of an adequate adsorption and comfortable garment when formed from a flat to an anatomically conforming condition.

A proportion skew factor of the absorbent pad length in the back region divided by the combined absorbent pad length of the central region plus the front region of the garment is less than about 0.10.

The undergarment provides an elastic means for facilitating the formation of a pouch structure in the central section, and an effective seal between the undergarment and the wearer.

The undergarment of the present invention is comfortable to wear and has preferred containment characteristics. A preferred embodiment of the present invention provides an absorbent pad facilitating rapid aqueous liquid transfer in the x, y, and z directions by a continuous and constant proportion of fiber and superabsorbent in the CD and MD directions throughout the dimensions of the absorbent pad.

In one aspect, the present invention provides a garment for use in absorbing and containing human body waste including a rectangular aqueous-liquid-impervious backing member having a peripheral edge, a rectangular aqueous-liquid-pervious body-side liner having a peripheral edge, wherein the body-side liner is joined to the backing member near the peripheral edges. In one aspect, the present invention provides a garment for use in absorbing and containing human body waste including a rectangular absorbent pad positioned between the body-side liner and the backing member.

A surge layer preferably contains large aqueous liquid gushes between the body-side liner and the absorbent pad. A pledget preferably is provided between the absorbent pad and the backing member. In one aspect, a pledget and a surge layer are provided and skewed into the front and central regions of the product and are not present in the back region.

By "aqueous-liquid-impervious" is meant a layer or laminate for containing aqueous liquid such as urine. The aqueous liquid will not pass through the layer or laminate under ordinary use in a direction perpendicular to the plane of the layer or laminate at the point of aqueous liquid contact.

Figure 2:
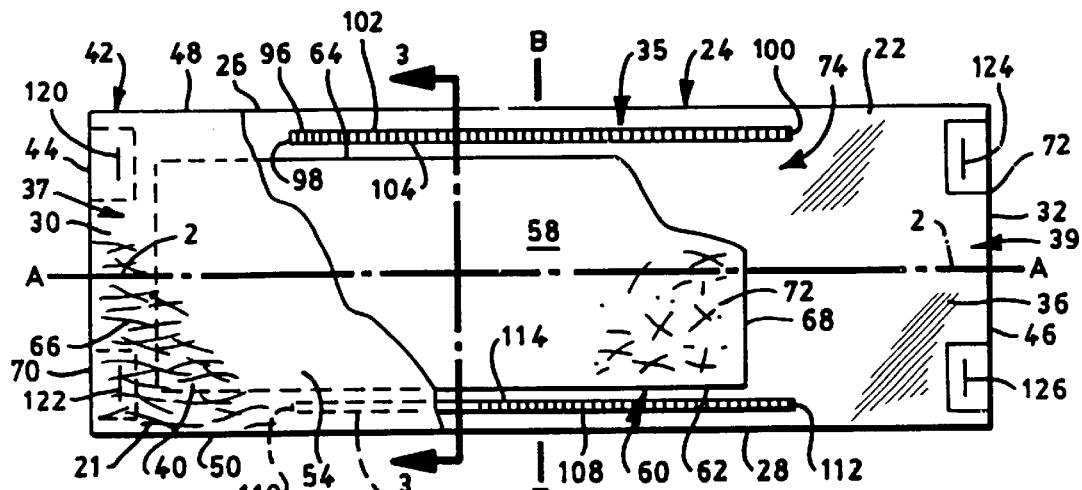
FIG. 2 is a plan view of the specific embodiment of FIG. 1 in an extended condition with the liquid pervious liner facing the viewer, and a portions of the liquid pervious liner and a portion of the absorbent layer removed.

The back, back side, or back portion with reference to the human anatomy is defined by reference to FIG. 2. FIG. 2 illustrates a transverse axis or plane passing through the center of the illustrated undergarment to divide it into a front half and a back half. The "back" or "back side" or "back portion" of the wearer will include that portion from the centerline on one side of the wearer and around the back to a similar point on the other side of the wearer.

Back region is the back one third of the total garment length which is worn on the posterior side of the wearer's body.

Barrier fabric or barrier means a fabric which is relatively impervious to the transmission of aqueous liquids, i.e., a fabric which has a blood strike-through rate of 1.0 or less according to ASTM test method 22.

Barrier fabric refers to a fabric having a useful level of resistance to penetration by aqueous liquid and/or particulates. Resistance to aqueous liquid penetration is measured by hydrostatic head tests, strike-through tests, and water spray penetration tests. A material with resistance to aqueous liquid penetration refers to a material having a hydrostatic head of at least about 20 centimeters as determined in accordance with the standard hydrostatic pressure test AATCCTM No. 127-1977. For example, an aqueous liquid resistant material has a hydrostatic head of 60 centimeters or more. Resistance to penetration by particulates is measured by determining the air filter retention of dry particles and is expressed as a particles holdout efficiency. Particle holdout efficiency refers to the efficiency of a material at preventing the passage of particles of a certain size range through the material. Particle holdout efficiency is measured by determining the air filter retention of dry particles utilizing IBR Test Method No. E-217, Revision G (Jan. 15, 1991) performed by InterBasic Resources, Inc. of Grass Lake, Mich. A high particle holdout efficiency is preferred for barrier fabrics. Preferably, barrier fabrics resist penetration by a column of tap water of at least about 20 cm and/or have a particle hold-out efficiency of at least about 40 percent for particles having a diameter greater than about 0.1 micron.

Blend means a mixture of two or more polymers, while the term "alloy" means a sub-class of blends wherein the components are immiscible but have been compatibilized. "Miscibility" and "immiscibility" are defined as blends having negative and positive values, respectively, for the free energy of mixing. Further, "compatibilization" is defined as the process of modifying the interfacial properties of an immiscible polymer blend in order to make an alloy.

Bonded refers to the joining, adhering, connecting, or attaching of two elements. Two elements are considered to be bonded together when they are bonded directly to one another or indirectly to one another, such as when each is bonded directly to intermediate elements.

Bonded carded web refers to webs made from staple fibers sent through a combing or carding unit, which breaks apart and aligns the staple fibers in the machine direction to form a machine-direction oriented fibrous nonwoven web. Such fibers are purchased in bales placed in a picker which separates the fibers prior to the carding unit. When the web is formed, it then is bonded by one or more of several known bonding methods. One such bonding method is powder bonding. A powdered adhesive is distributed through the web and then activated by heating the web and adhesive with hot air. Another bonding method is pattern bonding. A heated calender roll or ultrasonic bonding equipment bonds the fibers together in a localized bond pattern, though the web can be bonded across its entire surface. Through-air bonding is used for bonding bicomponent staple fibers.

Bulk refers to the thickness of samples measured with a Model 49-70 thickness tester available from TMI (Testing Machines Incorporated) of Amityville, N.Y. The thickness tester was equipped with a 2-inch diameter circular foot and measurements were taken at an applied pressure of about 0.2 pounds per square inch (psi). Bulk measurements of dry samples, i.e., having a moisture content less than about 10 percent, by weight, is referred to as dry bulk.

CD direction is the cross or short direction of the product and is perpendicular to the MD direction machine direction.

Cellulosic fibers refer to fibers including cellulose, a linear, water-wettable polysaccharide, whether existing as a single constituent in a larger natural aggregate such as wood pulp, bagasse and cotton linters, or as a derivative of the natural aggregate such as alpha pulp or viscose rayon.

Central region is the central one third of the total garment length between the front and back regions of the product on the wearer's body.

Closely adjacent means one element is positioned as close to another element as can be accomplished feasibly because of other nearby structure, manufacturing restraints, comfort, or fit considerations.

Coform means a process in which at least one meltblown die head is arranged near a chute through which other materials are added to the web while it is forming. Such other materials are pulp, superabsorbent particles, cellulose, or staple fibers, for example. Coform processes are shown in commonly assigned U.S. Pat. No. 4,818,464 to Lau and U.S. Pat. No. 4,100,324 to Anderson et al. Webs produced by the coform process are generally referred to as coform materials.

Consisting essentially of does not exclude the presence of additional materials which do not significantly affect the desired characteristics of a given composition or product. Exemplary materials of include, without limitation, pigments, antioxidants, stabilizers, surfactants, waxes, flow promoters, particulates, and materials added to enhance processability of the composition.

Continuous means that the described structure is a closed-loop structure. The continuous structure is unitary, i.e., a one-piece structure, or is made up of individual elements joined together to form a closed-loop.

Disposable means that the described garment or article is used until soiled, either by urination, defecation, or otherwise, and then discarded, rather than being washed and reused again. Disposable is not limited to single use or limited use articles but also refers to articles so inexpensive to the consumer that they can be discarded if they become soiled or otherwise unusable after only one or a few uses.

Disposed, disposed on, disposed with, disposed at, or disposed near are intended to mean that one element can be integral or unitary with another element or that one element can be a separate structure joined to, connected to, placed with, or placed near another element.

Elastic or elastomeric when referring to a fiber, film, or fabric means a material which upon application of a biasing force is stretchable to a stretched, biased length at least about 150 percent or one and a half times its relaxed, unstretched length, and which will recover at least 50 percent of its elongation upon release of the stretching, biasing force.

Elasticity, elastic, or elasticized refers to a property of a material or composite elastic material permitting it to recover at least a portion of its original size and shape after removal of the force causing the deformation, expressed in %.

Elasticizable describes a temporarily inhibited elasticized or elastic member which can be activated to recover its elasticity.

Elasticized means a naturally non-elastic material is rendered elastic by joining it to an elastic material.

Elongation means the ratio of the extension of a material to the length of the material prior to the extension, expressed as a percent, as represented by the following: extended length−original length/original length×100.

Extensible, elongatable, stretch, stretchability, or stretch characteristics, means a material which can have its length increased, expressed in units of length.

Extension, extend, or extended refers to an increased change in length of a material because of stretching and is expressed in units of length.

Fabric is used to refer to all of the woven, knitted, and nonwoven webs.

Filament refers to an element having a high ratio of length to diameter or width and includes a fiber, thread, strand, yarn or combination of a fiber, thread, strand, or yarn.

Finished product means a product manufactured for its intended purpose.

Flexible refers to materials which are compliant and readily conform to the shape and contours of a human body.

Front, front side, or front portion include the front part of an article or garment complementary to the "back" or "back side" or "back portion."

Front or back designate relationships relative to the garment itself, rather than to suggest any position the garment assumes when it is positioned on a wearer.

Front Region is the forward one third of the total garment length worn on the anterior side of the wearer's body.

Fully gathered with reference to an opening or border, for example, means that the material about the opening or border is gathered along its total periphery.

Garment means any type of worn non-medically oriented apparel, including industrial work wear and coveralls, undergarments, pants, shirts, jackets, gloves, and socks. Garment means any type of worn apparel, including industrial work wear and coveralls, undergarments, pants, shirts, jackets, gloves, and socks.

Hydrophilic describes fibers or surfaces of fibers wetted by the aqueous liquids in contact with the fibers. The degree of wetting of the materials is described in terms of contact angles and the surface tensions of the liquids and materials involved. Equipment for measuring the wettability of particular fiber materials or blends of fiber materials is provided by a Cahn SFA-222 Surface Force Analyzer System. When measured with this system, fibers having contact angles less than 90° are designated "wettable," i.e., "hydrophilic," and fibers having contact angles greater than 90° are "nonwettable," i.e., "hydrophobic."

Intake layer, intake material, or surge layer refers to a material to decelerate and diffuse surges of aqueous liquid introduced to the absorbent pad. Examples of these materials are described in U.S. Pat. No. 5,192,606 issued Mar. 9, 1993, to D. Proxmire et al.; U.S. Pat. No. 5,486,166 issued Jan. 23, 1996 to Ellis et al.; U.S. Pat. No. 5,490,846 issued Feb. 13, 1996 to Ellis et al.; and U.S. Pat. No. 5,509,915 issued Apr. 23, 1996 to Hanson et al.; the disclosures of which hereby are incorporated by reference.

Integral is refers to portions of a single unitary element rather than separate structures bonded to, placed with, placed near one another.

Inward or outward refers to positions relative to the center of an absorbent garment and transversely and/or longitudinally closer to or away from the longitudinal and transverse center of the absorbent garment.

Joining, join, or joined, when used in describing the relationship between two or more elements, means that the elements is connected together in any suitable manner, such as by heat sealing, ultrasonic bonding, thermal bonding, adhesives, or stitching. Further, the elements can be joined directly together or may have one or more elements interposed between them, all of which are connected together.

Layer when used in the singular can have the dual meaning of a single element or a plurality of elements.

Liquid means a substance and/or material that flows and will assume the interior shape of a container into which it is poured or placed. For this specification, aqueous liquid means an aqueous material that flows and will assume the interior shape of a container into which it is poured or placed.

Liquid communication or liquid migration refers to the ability of an aqueous liquid to travel through, between, or along two structures in the absence of an aqueous-liquid-impervious barrier preventing aqueous liquid travel between or along the two structures.

Liquid impervious when used in describing a layer or laminate including at least one aqueous-liquid-impervious film or layer and at least one U.S. patent film or layer means that the aqueous liquid will not pass through the laminate, under ordinary use conditions, in a direction generally perpendicular to the plane of the laminate at the point of aqueous liquid contact. Liquid may spread or be transported parallel to the plane of the aqueous-liquid-impervious film or layer, but is not considered to be within the meaning of "aqueous-liquid-impervious" when used with reference to the laminate.

Machine direction or MD means the length of a fabric in the direction in which it is produced. The term "cross machine direction" or CD means the width of fabric, i.e. a direction generally perpendicular to the MD.

MD direction is the longitudinal or long direction of the product and is typically the direction in which the product is manufactured.

Member when used in the singular can have the dual meaning of a single element or a plurality of elements.

Microfibers mean small diameter fibers having an average diameter not greater than about 75 microns, for example, having an average diameter of from about 0.5 microns to about 50 microns, or more particularly, microfibers have an average diameter of from about 2 microns to about 40 microns. An expression of fiber diameter is denier, defined as grams per 9000 meters of a fiber and calculated as fiber diameter in microns squared, multiplied by the density in grams/cc, multiplied by 0.00707. A lower denier indicates a finer fiber, and a higher denier indicates a thicker or heavier fiber. A diameter of a polypropylene fiber given as 15 microns is converted to denier by squaring, multiplying the result by 0.89 g/cc and multiplying by 0.00707. A micron polypropylene fiber has a denier of about 1.42 (152×0.89×0.00707=1.415). Outside the United States the unit of measurement is the "tex," is defined as the grams per kilometer of fiber. Tex is calculated as denier/g.

Monocomponent fiber refers to a fiber formed from one or more extruders using only one polymer, and is not meant to exclude fibers formed from one polymer to which small amounts of additives have been added for coloration, anti-static properties, lubrication, or hydrophilicity. Additives, e.g., titanium dioxide for coloration, are present in an amount less than 5 weight percent, e.g., at about 2 weight percent.

Multilayer laminate means a laminate wherein some of the layers are spunbond and some are meltblown such as a spunbond/-meltblown/spunbond (SMS) laminate and others as disclosed in U.S. Pat. No. 4,041,203 to Brock et al., U.S. Pat. No. 5,169,706 to Collier et al, U.S. Pat. No. 5,145,727 to Potts et al., U.S. Pat. 5,178,931 to Perkins et al., and U.S. Pat. No. 5,188,885 to Timmons et al. Such a laminate is made by sequentially depositing onto a moving forming belt first a spunbond fabric layer, then a melt-blown fabric layer, and last another spunbond layer, and then bonding the laminate. Alternatively, the fabric layers are made individually, collected in rolls, and combined in a separate bonding step. Such fabrics have a basis weight of from about 0.1 to 12 osy (6 to 400 gsm), or more, preferably from about 0.75 to about 3 osy. Multilayer laminates have various numbers of meltblown layers or multiple spunbond layers in different configurations and include other materials, films (F), or coform materials, e.g., SMMS, SM, SFS.

Non-elastic refers to a material which does not fall within the definition of "elastic."

Nonwoven fabric or nonwoven web means a web having a structure of individual fibers or threads which are interlaid, but not in an identifiable manner as in a knitted fabric. Nonwoven fabrics or webs have been formed from many processes such as, for example, meltblowing processes, spunbonding processes, and bonded carded web processes. The basis weight of nonwoven fabrics is expressed in ounces of material per square yard (osy) or grams per square meter (gsm), and the fiber diameters are expressed in microns. To convert from osy to gsm, multiply osy by 33.91.

Nonwoven web means a web of material formed without the aid of a textile weaving or knitting process, or a web having a structure of individual fibers or threads that are interlaid, but not in any identifiable, repeating pattern. Nonwoven webs have been formed by a variety of processes such as, for example, meltblowing processes, spunbonding processes, and bonded carded web processes. Nonwoven web means a web of material formed without the aid of a textile weaving or knitting process. Nonwoven webs have been formed from many processes such as, for example, meltblowing processes, spunbonding processes, and bonded carded web processes. The basis weight or nonwoven fabrics is expressed in ounces of material per square yard (osy) or grams per square meter (gsm) and the fiber diameters are expressed in microns.

Operatively joined, elastically associated, or associated with reference to the attachment of an elastic member to another element means that the elastic member when attached to or placed with or formed from the element gives that element elastic properties. With reference to the attachment of a non-elastic member to another element, it means that the member and element can be attached or placed together in any suitable manner that allows or permits them to perform their intended or described function, while not completely inhibiting the properties of the individual elements. The attaching or placing can be either directly, such as attaching or placing either member directly with an element, or can be indirectly by means of another member or element disposed between the first member and the first element. In the joining of an elastic member to a non-elastic member, the two joined members can exhibit elasticity or elastic properties. Operatively joined, with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

Outward refers to a position relative to the center of an absorbent garment, and particularly transversely and/or longitudinally away from the longitudinal and transverse center of the absorbent.

Partially elastic refers to a substrate, garment, a part of a garment, or the like, having at least one portion thereof that is elastic.

Particles as in SAP or SAM means any geometric or non-geometric form such as, but not limited to, spherical grains, cylindrical fibers or strands, flat surfaces or roughened surfaces, sheets, ribbons, strings, strands, or the like. When used in an absorbent structure, the particles can be loosely formed into a shaped structure or compressed into a shaped form.

Permeable or permeability or pervious refers to the ability of a aqueous liquid, such as, for example, a gas to pass through a particular porous material. Permeability is expressed in units of volume per unit time per unit area, for example, cubic feet per minute per square foot of material, e.g., $ft^3/minute/ft^2$. Permeability was determined utilizing a Frazier Air Permeability Tester available from the Frazier Precision Instrument Company and measured in accordance with Federal Test Method 5450, Standard No. 191A, except that the sample size was 8"×8" instead of 7"×7". Although permeability is expressed as the ability of air or other gas to pass through a permeable sheet, sufficient levels of gas permeability may correspond to levels of aqueous liquid permeability to enable the practice of the present invention. For example, a sufficient level of gas permeability may allow an adequate level of aqueous liquid to pass through a permeable sheet with or without assistance of a driving force such as, for example, an applied vacuum or applied gas pressure.

Personal care product means diapers, training pants, absorbent underpants, adult incontinence products, and feminine hygiene products.

Polymer includes but is not limited to, homopolymers, copolymers, such as for example, block, graft, random and alternating copolymers, terpolymers, and blends and modifications thereof. Unless otherwise specifically limited, the term "polymer" includes all geometrical configurations of the molecule. Configurations include, but are not limited to isotactic, syndiotactic, and random symmetries.

Pulp refers to pulp containing fibers from natural sources such as woody and non-woody plants. Woody plants include, for example, deciduous and coniferous trees. Non-woody plants include, for example, cotton, flax, esparto grass, milkweed, straw, jute hemp, and bagasse.

Releasably attached, releasably bonded, releasably engaged or variations thereof refer to two elements being connected or connectable such that the elements tend to remain connected absent a separation force applied to one or both of the elements, and the elements being capable of separation without substantial permanent deformation or rupture. The required separation force is beyond that encountered while wearing the absorbent garment.

Retraction refers to a decreasing change in length of an extended material upon removal of the force causing the extension.

Side refers to a position in which a side of the body faces the supporting surface.

Spunbonded fibers refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns.

Staple fiber refers to a natural fiber or a length cut from, for example, a manufactured filament. Staple fibers typically have a length between about 3 and about 7.5 millimeters.

Stretch, stretchability, or stretch characteristics mean that the material can have its length increased, expressed in units of length. See also Extensible.

Stretch bonding refers to a process wherein an elastic member is bonded to another member while only the elastic member is extended at least about 25 percent of its relaxed length. "Stretch bonded laminate" refers to a composite elastic material made according to the stretch bonding process, i.e., the layers are joined together when only the elastic layer is in an extended condition so that upon relaxing the layers, the nonelastic layer is gathered. Such laminates usually have machine directional stretch properties and are stretched to the extent that the nonelastic material gathered between the bond locations allows the elastic material to elongate. One type of stretch bonded laminate is disclosed, for example, by U.S. Pat. No. 4,720,415 to Vander Wielen et al., in which multiple layers of the same polymer produced from multiple banks of extruders are used. Other composite elastic materials are disclosed in U.S. Pat. No. 4,789,699 to Kieffer et al., U.S. Pat. No. 4,781,966 to Taylor and U.S. Pat. Nos. 4,657,802 and 4,652,487 to Morman and U.S. Pat. No. 4,655,760 to Morman et al.

Substrates, surface, or sheet means a layer that is a film or woven web or nonwoven web, a laminate, pervious or impervious to air, gas, and/or aqueous liquids; or a composite structure comprising for example a topsheet, backsheet, and an absorbent medium between the topsheet and backsheet.

Superabsorbent refers to absorbent materials capable of absorbing at least 10 grams of aqueous liquid, e.g., distilled water per gram of absorbent material while immersed in the liquid for 4 hours and holding substantially all of the absorbed aqueous liquid while under a compression force of up to about 1.5 psi.

Surface includes any layer, film, woven, nonwoven, laminate, composite, or the like, whether pervious or impervious to air, gas, and/or aqueous liquids.

Surge layer refers to a material designed to help decelerate and diffuse surges of aqueous liquid that are introduced to the absorbent pad. Examples of surge materials are described in U.S. Pat. No. 5,192,606 issued Mar. 9, 1993, to D. Proxmire et al.; U.S. Pat. No. 5,486,166 issued Jan. 23, 1996 to Ellis et al.; U.S. Pat. No. 5,490,846 issued Feb. 13, 1996 to Ellis et al.; and U.S. Pat. No. 5,509,915 issued Apr. 23, 1996 to Hanson et al.; the disclosures of which are hereby incorporated by reference.

Tension refers to a force tending to cause the extension of a body, or to the balancing force within that body resisting the extension. Tension is expressed in units of grams.

Thermoplastic means a material that softens when exposed to heat and which substantially returns to a non-softened condition when cooled to room temperature.

Through-air bonding or TAB means a process of bonding a nonwoven bicomponent fiber web in which air, sufficiently hot to melt one of the polymers of which the fibers of the web is forced through the web. The air velocity is between 100 and 500 feet per minute, and the dwell time is as long as 6 seconds. The melting and resolidification of the polymer provides the bonding. Through air bonding has relatively restricted variability. Through-air bonding TAB requires the melting of at least one component to accomplish bonding, and is restricted to webs with two components like conjugate fibers or those which include an adhesive. In the through-air bonder, air having a temperature above the melting temperature of one component and below the melting temperature of another component is directed from a surrounding hood, through the web, and into a perforated roller supporting the web. Alternatively, the through-air bonder is a flat arrangement wherein the air is directed vertically downward onto the web. The operating conditions of the two configurations are similar, the primary difference being the geometry of the web during bonding. The hot air melts the lower melting polymer component and thereby forms bonds between the filaments to integrate the web.

Two-dimensional refers to a garment, such as a diaper, that can be opened and laid in a flat condition without destructively tearing any structure. A two-dimensional garment does not have continuous leg and waist openings when opened and laid flat and requires a refastening device, such as adhesive tapes, to attach about the wearer.

Undergarment refers to a substantially rectangular adult incontinence absorbent product suspended from the wearer by straps attached to the waist regions of the product. Examples are commercially available DEPEND® Elastic Leg Underpants products.

Figure 1:
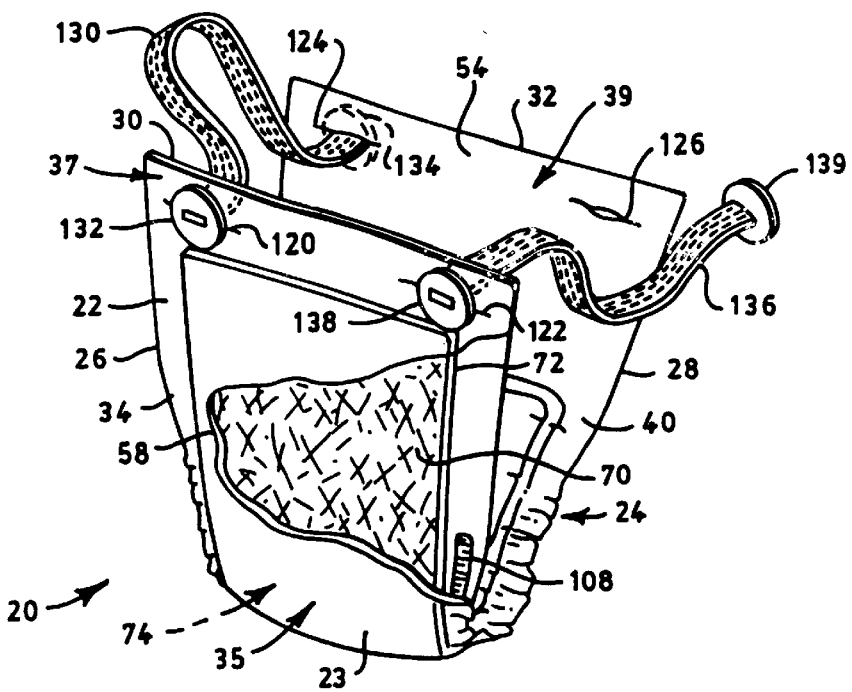
FIG. 1 is a perspective view of a specific embodiment of the invention with a portion of the liquid impervious backing removed to expose the interior structure of the embodiment.
Figure 3:
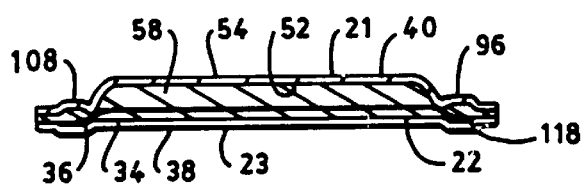
FIG. 3 is a cross-sectional view of the specific embodiment of FIG. 2 taken along section line 3—3 of FIG. 2.

Referring now to FIGS. 1 through 3, an absorbent garment of the present invention includes an aqueous-liquid-impervious backing member 22 of rectangular shape. The absorbent garment 20 has a peripheral edge 24, side edges 26 and 28, a front edge 30, and a back edge 32.

The absorbent garment 20 includes a backing member 22, a substantially aqueous-liquid-pervious body-side liner 40, and an absorbent pad 58 sandwiched between the backing member 22 and the body-side liner 40 superimposed on the outer member 38. See FIGS. 1, 2, 3, 3a, 4a, 4b, and 4c. An undergarment as shown in the drawings of the Figures is one embodiment of the present invention. The backing member 22 and the body-side liner 40 preferably are longer and wider than the absorbent pad 58, so that the peripheries of the backing member 22 and the body-side liner 40 form margins sealed together using ultrasonic bonds, thermal bonds, or adhesives. In this sealed area, the leg elastics 96 and 108 are incorporated between the backing member 22 and the body-side liner 40. The absorbent pad 58 is attached to the backing member 22 and/or the body-side liner 40 using ultrasonic bonds or adhesives. See FIGS. 1 and 2. The absorbent garment 20 also includes an outer member 38. The outer member 38 is attached to the backing member 22 using ultrasonic bonds or adhesives. The body-side liner 40 is positioned toward the wearer and is the body-facing surface 21 of the undergarment 20. Conversely, the backing member 22 is positioned toward the outer member 38 and the outer clothing of the wearer and is the garment-facing surface 23 of garment 20.

The garment 20 is constructed by supplying the body-side liner 40 and the backing member 22 materials and sandwiching an individual absorbent pad 58 between the backing member 22 and the body-side liner 40. The side and end peripheries of the backing member 22 and the body-side liner 40 outward of the absorbent pad 58 are joined, forming the central region 35, the front region 37, and the back region 39, and sealed together.

Referring now to FIGS. 8, 9, 10, 11, and 12, the central region 35 is the center one third of the total product length falling between lines 4—4 and 5—5. The front region 37 is the one third of the total product length of the garment 20 between line 4—4 and the front end edge 30 of the garment 20 and is worn against the anterior side of the wearer's body. The back region 39 of the garment 20 is that one third of the length of the garment 20 between line 5—5 and the back end edge 32 of the garment 20 and is worn against the posterior side of the wearer's body. The absorbent pad 58 is T-shaped, I-shaped, oval-shaped, hourglass-shaped, rectangular-shaped, or irregularly-shaped. The absorbent pad 58 also includes leg cutouts 900, opposing indentations in the longitudinal sides 62 and 64 of the absorbent pad 58. The leg cutouts 900 enhance the fit of the garment 20 as the reduced bulk between the wearer's legs reduces or prevents gapping, thereby preventing leaks and improving comfort. The other materials used in the garment 20, including but not limited to the body-side liner 40, the backing member 22, and outer member 38, also are shaped to include leg cutouts 900.

It is preferred for the absorbent pad 58 to be shaped to include leg cutouts 900, and not shape the other materials, including the body-side liner 40, the backing member 22, and the outer member 38, to include leg cutouts 900. The absorbent pad 58, leg cutouts 900, and leg elastic 96 and 108 are not placed symmetrically in garment 20 but are skewed toward the front end edge 30 of garment 20.

The article of the present invention includes geometric shapes of rectangular, oval or racetrack patterns, hourglass configurations, and bi-lobal shapes, where the length is greater or less than the width.

The backing member 22 prevents aqueous liquid strike-through to the outer clothing when discharge occurs onto the absorbent pad 58 of the garment 20. The backing member 22 is located on the inside of the outer member 38 of the garment 20 and includes an aqueous-liquid-impervious film such as polyethylene. The aqueous-liquid-impervious backing member 22 has an exterior surface 34 facing away from the wearer and an interior surface 36 facing toward the wearer. In construction of the garment 20, the backing member 22 acting as a barrier retards the movement of the aqueous liquid through the garment 20 by making the backing member 22 resistant to penetration encountered under wearing conditions. The backing member 22 preferably includes a material formed or treated to be aqueous-liquid impervious. Alternatively, the backing member 22 includes an aqueous-liquid-pervious material. An aqueous-liquid-impervious layer associated with the absorbent pad 58 is provided to impede aqueous-liquid movement away from the absorbent pad 58. The garment 20 is rendered aqueous-liquid impervious by coating the absorbent pad 58 or by securing a separate aqueous-liquid-impervious material to the absorbent pad 58. The backing member 22 includes a thin, aqueous-liquid-impervious web or sheet of plastic film such as polyethylene, polypropylene, or polyvinyl chloride. Other acceptable materials include a single spunbonded layer, two layers of spunbonded and meltblown materials, or a three-layer material of spunbonded-meltblown-spunbonded material. Foam materials are used, and materials both aqueous-liquid impervious and vapor pervious.

Alternately, the backing member 22 includes a nonwoven, fibrous web constructed and arranged to have low aqueous-liquid perviousness. Still alternately, the backing member 22 includes a layered or laminated material, such as a thermally bonded plastic film and nonwoven web composite. Alternatively, the backing member 22 includes a aqueous-liquid-impervious film or foam pervious to water vapor under normal wearing conditions. More preferred, the backing member 22 has a water vapor transmission rate of at least about 800 grams/m$^2$/24 hours measured by ASTM E96-92. One example of a suitable film is a 39.4 grams per square meter microporous film produced by Mitsui and sold by Consolidated Thermoplastics (CT) under the trade name of ESPOIR® N-TAF-CT.

The outer member 38 is compliant and soft feeling to the wearer. The outer member 38 is a soft, flexible, porous sheet aqueous-liquid pervious, permitting aqueous liquids to penetrate readily into its thickness, or impervious, resistant to the penetration of aqueous liquids into its thickness. A suitable outer member 38 is manufactured from a wide range of materials, such as natural fibers, e.g., wood or cotton fibers, synthetic fibers, e.g., polyester or polypropylene fibers, or from a combination of natural and synthetic fibers or reticulated foams and apertured plastic films.

The outer member 38 is a woven web or sheet, or a nonwoven web or sheet such as a spunbond, meltblown or bonded-carded web of synthetic polymer filaments, such as polypropylene, polyethylene, or polyesters, a web of natural polymer filaments such as rayon or cotton. The bonded-carded web is thermally bonded or sprayed with a fabric binder. The outer member 38 is a nonwoven spunbond. The outer member 38 is a spunbond polypropylene nonwoven with a wireweave bond pattern. The spunbond material is available from Kimberly-Clark Corporation, located in Roswell, Ga. The outer member 38 has a weight from about 0.3 oz. per square yard (osy) to about 2.0 osy and alternatively about 0.6 osy. The outer member 38 of the garment 20 is printed, colored, or decoratively embossed. The outer member 38 has a pore size allowing the passage of air, sweat, and perspiration because of the breathability of the material. The outer member 38 is selectively embossed or perforated with discrete slits or holes.

The garment 20 further includes a rectangular aqueous-liquid-pervious body-side liner 40 of approximately the same dimension as aqueous-liquid-impervious backing member 22. See FIGS. 2, 3, and 3a. The aqueous-liquid-pervious body-side liner 40 has a peripheral edge 42 including a front edge 44, a back edge 46, and side edges 48 and 50. The aqueous-liquid-pervious body-side liner 40 has an exterior surface 52 facing away from the wearer and an interior surface 54 that facing the wearer.

The body-side liner 40 includes a nonwoven or other soft material for contacting the wearer's skin. The body-side liner 40 is compliant and soft feeling to the wearer. The body-side liner 40 a soft, flexible, porous sheet which is aqueous-liquid-pervious, permitting aqueous liquids to penetrate readily into its thickness. A suitable body-side liner 40 is manufactured from a wide range of materials, such as natural fibers, e.g., wood or cotton fibers, synthetic fibers, e.g., polyester or polypropylene fibers, or from a combination of natural and synthetic fibers or reticulated foams and apertured plastic films.

The body-side liner 40 is formed of a aqueous-liquid-pervious material so that aqueous liquid waste, and possibly semisolid waste, passes through to the absorbent pad 58 and is absorbed by the absorbent pad 58. A suitable body-side liner 40 is a nonwoven web, a spunbond, meltblown, or bonded-carded web composed of synthetic polymer filaments or fibers, such as polypropylene, polyethylene, or polyesters, a perforated film, or a web or natural polymer filaments or fibers such as rayon or cotton. The body-side liner 40 is treated with a surfactant to aid in aqueous liquid transfer. The body-side liner 40 is a nonwoven spunbond. The spunbond material is available from Kimberly-Clark Corporation, located in Roswell, Ga. The body-side liner 40 has a weight from about 0.3 oz. per square yard (osy) to about 2.0 osy and alternatively about 0.5 osy. The body-side liner 40 of the underpant maybe printed, colored, or decoratively embossed. The body-side liner 40 also is a nonwoven web or sheet of polyolefin fibers, such as polypropylene, polyester, polyethylene, Rayon, and Chisso. The body-side liner 40 also is a plastic film with perforations, an expanded plastic webbing material or a scrim material. The body-side liner 40 has a pore size allowing the passage of air, sweat, and perspiration because of the breathability of the material. The body-side liner 40 is embossed or perforated selectively with discrete slits or holes.

The fabric of the body-side liner 40 is surface treated with a surfactant commercially available from Union Carbide Chemicals and Plastics Company, Inc., of Danbury, Conn., U.S.A. under the trade designation TRITON X-102. As used herein, the term "fabric" refers to all of the woven, knitted, and nonwoven fibrous webs. The term "nonwoven web" means a web of material that is formed without the aid of a textile weaving or knitting process.

As an alternate material, an aqueous-liquid-pervious body-side liner 40 is made of a carded web of polyester fibers bonded to a spunbonded polypropylene or polyethylene carrier sheet. The carded material is made up of about 20 to about 60 weight percent polypropylene or polyethylene and about 80 to about 40 weight percent polyester. The basis weight is between about 30 gsm and about 70 gsm.

The aqueous-liquid-impervious backing member 22 and aqueous-liquid-pervious body-side liner 40 are joined near their respective peripheral edges 24 and 42 to form a container, designated as 74, having an interior volume of the garment 20. The interior volume of container 74 contains the remaining structure of the garment 20, which includes an absorbent pad 58.

The aqueous-liquid-impervious backing member 22 and the aqueous-liquid-pervious body-side liner 40 have the same width and length. The width of the backing member 22 and the body-side liner 40 ranges between about 4 inches (102 mm) and 10 inches (254 mm), more preferably between about 5 inches (127 mm) and about 10 inches (254 mm), and most preferably between about 5 inches (127 mm) and about 9 inches (229 mm). The length of backing member 22 and the body-side liner 40 ranges between about inches (381 mm) and 40 inches (1016 mm), more preferably between about 21 inches (533 mm) and about 29 inches (737 mm), most preferably between about 23 inches (584 mm) and about 28 inches (711 mm). In the specific embodiment of the invention as illustrated in FIGS. 1–3 and 3a, the width of the backing member 22 and the body-side liner 40 is about 9 inches (229 mm), and the length is about 27 inches (687 mm).

Referring to FIGS. 1, 2, 4a, and 4b, the absorbent pad 58 is of a rectangular shape and includes a peripheral edge 60 having side edges 62 and 64, a front end edge 66, and a back end edge 68. The absorbent pad 58 has an exterior surface 70 away from the wearer, and an interior surface 72 facing toward the wearer.

The porous fibrous matrix of absorbent pad 58 is preferably an air laid batt of fluff and high absorbency material formed according to Mazurak and Fries as set forth in U.S. Pat. No. 4,381,782, the entire disclosure of which is incorporated herein by reference.

Figure 5:
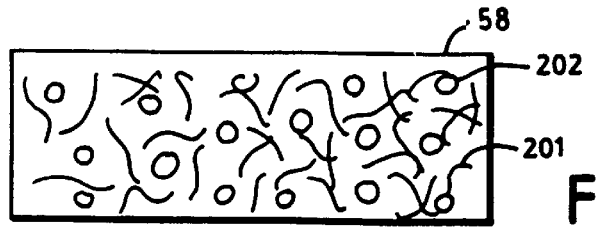
FIG. 5 is a cross-sectional view of the absorbent pad taken along section line 3—3 of FIG. 2 and which shows a homogeneous distribution of fibrous and high absorbency material.
Figure 5A:
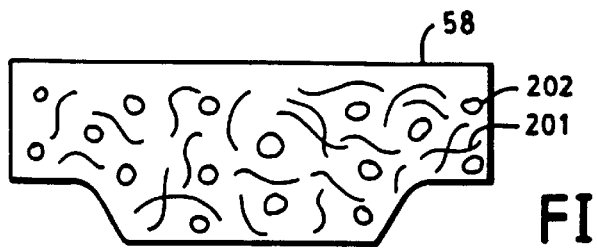
FIG. 5A is a cross-sectional view of the absorbent pad taken along section line 3—3 of FIG. 2 and which shows a homogeneous distribution of fibrous and high absorbency material which has a profiled basis weight distribution.
Figure 6:
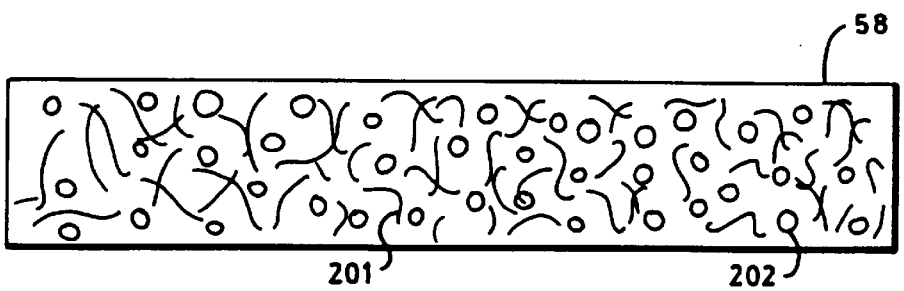
FIG. 6 is a cross-sectional view of the absorbent pad taken along section line 2—2 of FIG. 2 and which shows a homogeneous distribution of fibrous and high absorbency material.
Figure 7:
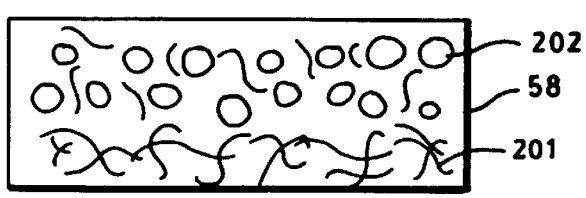
FIG. 7 is a cross-sectional view of the absorbent pad taken along section line 3—3 of FIG. 2 and which shows a layered distribution of fibrous and high absorbency material
Figure 7A:
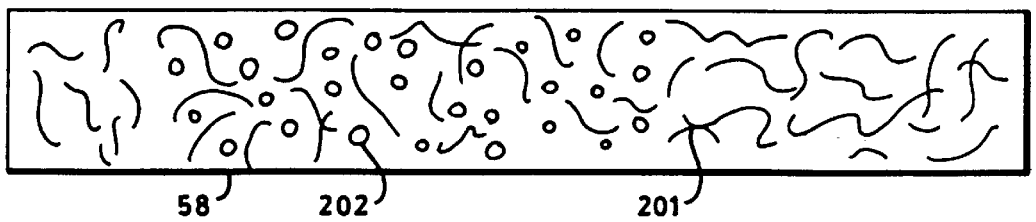
FIG. 7a is a cross-sectional view of the absorbent pad taken along section line 2—2 of FIG. 2 and which shows a pulsed distribution of fibrous and high absorbency material with little high absorbency material in the ends.
Figure 7B:
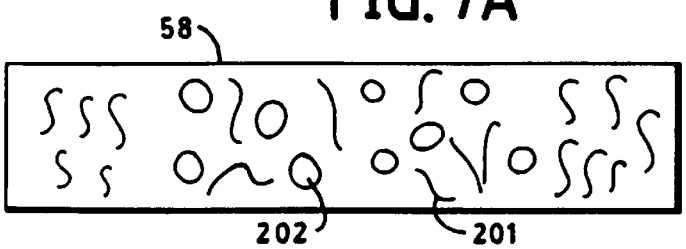
FIG. 7b is a cross-sectional view of the absorbent pad taken along section line 3—3 of FIG. 2 and which shows a non-uniform distribution of fibrous and high absorbency material in the cross direction of the absorbent pad.

Referring now to FIGS. 5, 5A, 6, 7, 7a, and 7b, the absorbent pad 58 includes an air-formed mixture of high absorbency material (SAP) 202 and fibers 201, preferably of fluff pulp. Most preferably, as shown in FIGS. 5, 5A, and 6, the mixing of the fluff fibers 201 and the high absorbency material 202 is homogeneous. Less preferably, as shown in FIGS. 7, 7a, and 7b, the mixtures are layered as in FIG. 7, phased to place the high absorbency material 202 in a specific machine direction location, as in FIG. 7a, or placed in a narrow band in the cross direction, as in FIG. 7b, or both. Also, the fibers 201, other than fluff pulp such as chemically stiffened and thermo-mechanical pulps, are used. The absorbent pad 58 includes absorbent material 201 other than air formed fluff 201 and SAP 202. For example, coform materials as referenced in U.S. Pat. No. 4,818,464 to Lau and U.S. Pat. No. 4,100,324 to Anderson are used to make the absorbent as long as they also contain high absorbency materials. In addition, wet formed composite materials including a combination of fibers and high absorbency materials as disclosed in U.S. Pat. No. 5,651,862 to Anderson et. al. are used. Stabilized air-laid materials including a mixtures of fibers, binder fibers, and high absorbency materials bound together by latex binding or through-air bonding also are usable as absorbent materials.

The high absorbency materials 202 are hydrogel polymers preferably sufficiently cross-linked to render the materials water-insoluble. Cross-linking is by irradiation or by covalent, ionic, van der Waals, or hydrogen bonding. Suitable materials 202 are available from various commercial vendors, such as Dow Chemical Company (Drytech 2035 LD), Hoechst-Celanese Corporation and Allied-Colloid. The high-absorbency material 202 is capable of absorbing at least about 15 times its weight in water, and preferably is capable of absorbing more than about 25 times its weight in water.

The high-absorbency material 202 is distributed or otherwise incorporated into the absorbent pad 58. For example, as illustrated in FIGS. 5, 6, 7, 7a, and 7b, the high-absorbency material 202 is distributed uniformly among the fibers 201 including the absorbent pad 58. The materials 202 also are distributed non-uniformly within the fibers 201 of the absorbent pad 58 to form a continuous gradient with either an increasing or decreasing concentration of high-absorbency material 202, as determined by observing the concentration moving inward from the backing member 22. Alternatively, the high-absorbency material include a discrete layer separate from the fibers 201 of the absorbent pad 58, or include a discrete layer integral with the absorbent pad 58.

Figure 3A:
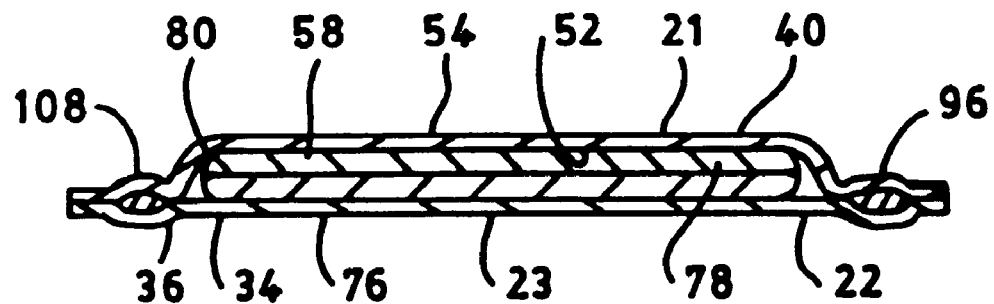
FIG. 3a is a cross-sectional view of an alternate embodiment of FIG. 2 taken along section line 3—3 of FIG. 2.

The absorbent pad 58 also includes a wrap layer 80 to maintain the integrity of the fibrous absorbent pad 58 (See FIG. 3a). The wrap layer 80 includes a cellulosic tissue or spunbond, meltblown, or bonded-carded web material composed of synthetic polymer filaments, such as polypropylene, polyethylene, or polyesters or natural polymer filaments such as rayon or cotton.

The absorbent pad 58 has an aqueous liquid capacity great enough to absorb discharges from about 10 grams to about 1500 grams. The absorbent pad 58 preferably has a capacity and a thickness preferably less than about 25 mm, thus providing a non-bulky and flexible fit. The capacity of the absorbent pad 58 has a total capacity of about 200 grams to about 1300 grams. Preferably, the absorbent pad 58 has a total capacity of at least about 300 grams and not more than about 1200 grams. More preferably, the total capacity of the absorbent pad 58 is from about 400 grams to about 800 grams.

The total capacity of the absorbent pad 58 is determined using the absorbent pad 58 of the garment 20, the body-side liner 40, the backing member 22, and the outer member 38. The saturated retention capacity is a measure of the total absorbent capacity of an absorbent garment 20, in this case an undergarment 20. The saturated retention capacity is determined as follows. The undergarment 20 to be tested, having a moisture content of less than about 7 weight percent, is weighed and submerged in an excess quantity of the room temperature (about 23° C.) saline solution described below. The material is allowed to remain submerged for 20 minutes. After 20 minutes the undergarment 20 is removed from the saline solution and placed on a Teflon™ coated fiberglass screen having 0.25 inch openings (commercially available from Taconic Plastics Inc., Petersburg, N.Y.) which, in turn, is placed on a vacuum box and covered with a flexible rubber dam material. A vacuum of 3.5 kilopascals (0.5 pounds per square inch) is drawn in the vacuum box for a period of 5 minutes. The undergarment 20 is weighed again. The amount of aqueous liquid retained by the material being tested is determined by subtracting the dry weight of the undergarment 20 from the wet weight of the undergarment 20 (after application of the vacuum) and is reported as the saturated retention capacity in grams of aqueous liquid retained.

The saline solution is an aqueous solution of about 0.9 percent sodium chloride by weight. A suitable product is S/P™ Certified Blood Saline commercially available from Baxter Diagnostics in McGaw Park, Ill.

The absorbent pad 58 includes materials adapted to absorb and retain urine, menses, blood, or other body excrement. The absorbent pad 58 includes various natural or synthetic absorbent materials, such as cellulose fibers, surfactant treated meltblown fibers, wood pulp fibers, regenerated cellulose or cotton fibers, a blend of pulp and other fiber, or the like. The absorbent pad 58 may also include compounds to increase its absorbency, such as 0–95 weight percent of organic or inorganic high-absorbency materials, which are preferably capable of absorbing at least about 15 and preferably more that 25 times their weight in water. Organic high-absorbency materials can include natural materials, such as pectin, guar gum and peat moss, as well as synthetic materials, such as synthetic hydrogel polymers. Such hydrogel polymers may include, for example, carboxymethylcellulose, alkali metal salts of polyacrylic acids, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, polyvinyl pyridine or the like. Other suitable polymers can include hydrolyzed acrylonitrile grafted starch, acrylic acid grafted starch, and isobutylene maleic anhydride copolymers, and mixtures thereof. Suitable high-absorbency materials are described in U.S. Pat. No. 4,699,823 issued Oct. 13, 1987, to Kellenberger et at. And U.S. Pat. No. 5,147,343 issued Sep. 15, 1992 to Kellenberger, which are incorporated herein by reference. High absorbency materials are available from various commercial vendors, such as Dow Chemical Company, Stockhausen, Inc., Hoechst Celanese Corporation, and Allied Colloids, Inc. The absorbent pad 58 may also include tissue layers or acquisition or distribution layers to help maintain the integrity of fibrous absorbents or transport aqueous liquids.

The absorbent undergarment 20 includes additional components to assist in the acquisition, distribution, and storage of body exudates. For example, the absorbent undergarment 20 may include a transport layer, such as described in U.S. Pat. No. 4,798,603 issued Jan. 17, 1989, to Meyer et al., or a surge management layer, such as described in U.S. Pat. No. 5,486,166 issued Jan. 23, 1996, to Bishop et al., U.S. Pat. No. 5,364,382 issued Nov. 15, 1994, to Latimer et al., U.S. Pat. No. 5,490,846 to Ellis et. al, U.S. Pat. No. 5,429,629 to Latimer et al., U.S. Pat. No. 5,509,915 to Hanson et.al., U.S. Pat. No. 5,192,606 to Proxmire et al., and European Patent Application EP 0 539 703 A1, published May 5, 1993, which the patents and application are incorporated herein by reference. Such layers are also referred to as acquisition/distribution layers. A surge layer is positioned within about 0 inch (0 cm) to about 4 inches (10.2 cm) from the front end edge 66 of the absorbent pad 58, more preferably from about 0 inch (0 cm) to about 2 inches (5.1 cm) from the front end edge 66 of the absorbent pad 58 and most preferably from about 0 inch (0 cm) to about 1 inch (2.5 cm) from the front end edge 66 of the absorbent pad 58.

The length of the surge layer is between about 5 inches (12.7 cm) and about 19 inches (48.3 cm), more preferably between about 8 inches (20.3 cm) and about 16 inches (40.6 cm), and most preferably between about 10 inches (25.4 cm) and about 14 inches (35.6 cm). The length of the surge layer is about 12 inches (30.5 cm).

The acquisition/distribution layer 78 is disposed on the aqueous liquid storage layer 76 toward the body-facing surface 21 of the absorbent pad 58 to decelerate and diffuse surges of aqueous liquid introduced into the absorbent pad 58. The acquisition/distribution layer 78 includes a through-air bonded carded web composed of a blend of 40 percent 6 denier polyester fibers, commercially available from Hoechst Celanese Corporation, and 60 percent 3 denier polypropylene/polyethylene sheath core bi-component fibers, commercially available from the Chisso Corporation, with an overall basis weight ranging of from about 50 gsm and about 120 gsm.

One absorbent pad 58 includes an aqueous liquid storage layer 76 in which the basis weight of the absorbent components, such as fluff, pulp, and superabsorbent (SAP), are continuous throughout the MD length of the absorbent pad 58. The distribution of the absorbent components is homogeneous in at least the y-direction, preferably in the x- and y-directions and is homogeneous in the z-direction within the absorbent pad 58. The basis weight of the absorbent pad 58 ranges between about 80 gsm and about 1,000 gsm. More preferably, an acquisition layer 78 is disposed in the aqueous liquid storage layer 76, which is moved forward on the aqueous-liquid-storage layer 78. The fluff pulp/SAP ratio ranges from about 100:0 to about 40:60, and more preferably from about 80:20 to about 50:50.

The absorbent pad 58 provides the feature to transport aqueous liquid in an x- and y-direction and in a z-direction. The transport of aqueous liquid in the z-direction is movement of a wicking nature and gravity flow where the aqueous liquid moves away from the body of the wearer. The transport of aqueous liquid in the x-direction and y-direction is movement and/or wicking of aqueous liquid along the length and width of the absorbent pad 58. The movement of aqueous liquid both away from the wearer and along the length and width of the absorbent pad 58 results in an increase in the utilization of the area of the absorbent pad 58 since the aqueous liquid moves towards the distal ends of the absorbent pad 58, and the result is an improvement of the absorption characteristics of the absorbent pad 58.

Figure 4C:
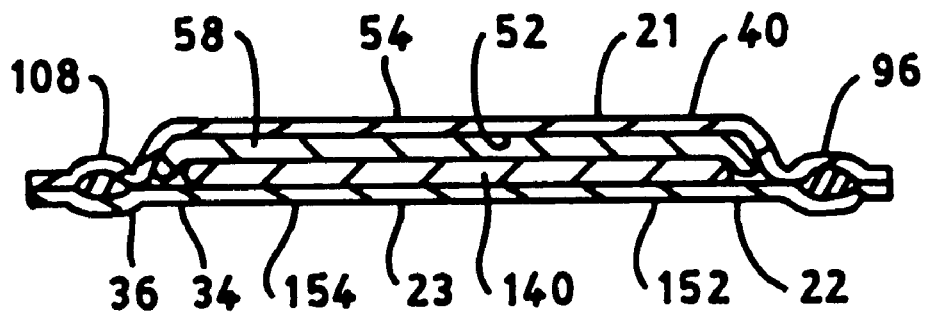
FIG. 4a is a perspective view of the specific embodiment of the invention with a portion of the liquid impervious backing removed to expose the interior structure of the embodiments.
FIG. 4b is a plan view of the specific embodiment of FIG. 4a in an extended condition with the liquid pervious liner facing the viewer, and a portions of the liquid pervious liner and a portion of the absorbent layer removed, and, FIG. 4c is a cross-sectional view of the specific embodiment of FIG. 2 taken along section line 3—3 of FIG. 4b.
Figure 4A:
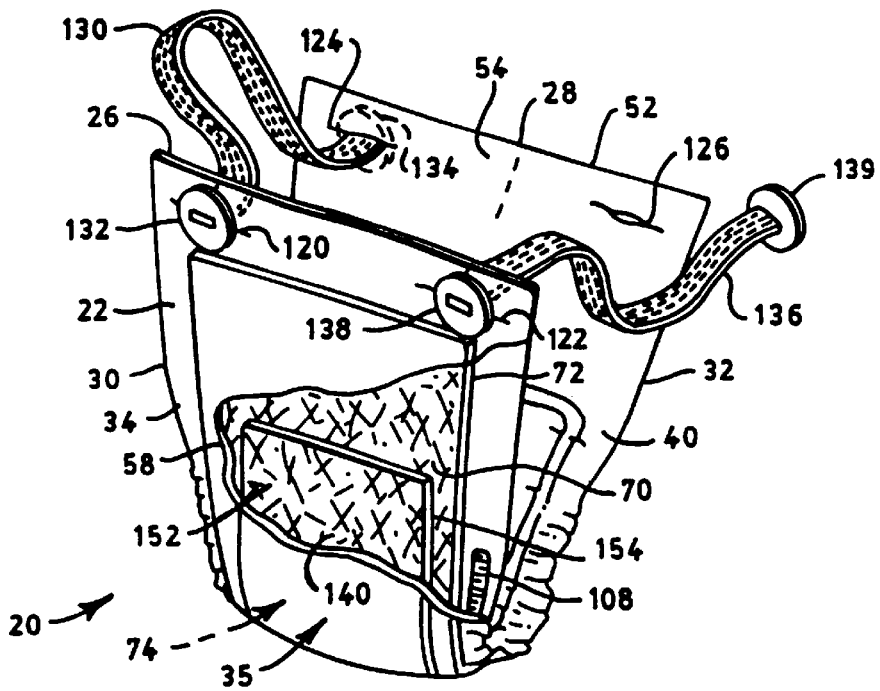
Figure 4B:
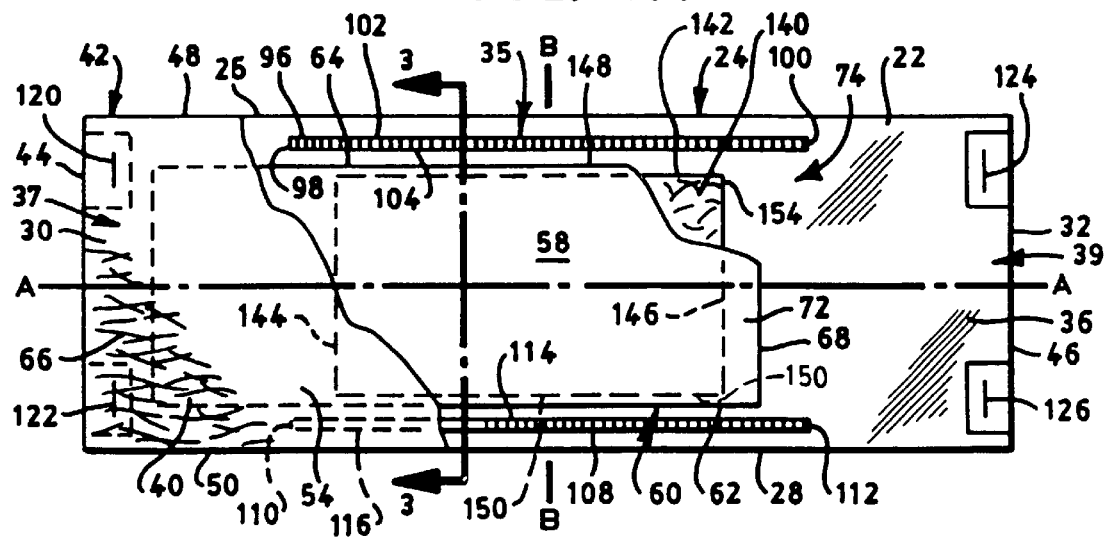

As illustrated in FIGS. 2 and 4b, the absorbent pad 58 has a width measured between the side edges 62 and 64. The absorbent pad 58 has a length measured between the front end and the back end edges 66 and 68. The width and length of the absorbent pad 58 are each less than the corresponding width and length of the container 74 comprised of the backing member 22 and the aqueous-liquid-pervious body-side liner 40. The width of container 74 is measured between the side edges 26 and 28 of the garment 20 thereof, and the length of the container 74 is measured between the front and back edges 30 and 32 of the garment 20.

The overall length of the absorbent pad 58 prevents aqueous liquid leakage when sleeping or sitting. The overall length is at least about 12 inches (305 mm) thus extending beyond the central region 35 along the longitudinal centerline A—A of the undergarment 20. Alternatively, the length should be in the range of about 12 inches (305 mm) to about 30 inches (762 mm), more preferably ranging from about 15 inches (381 mm) to about 23 inches (584 mm). A preferred range is from about 15 inches (381 mm) to about 21 inches (533 mm) in length, more preferably ranging from about 17 inches (432 mm) to about 20 inches (508 mm). The preferred length of the absorbent pad 58 is about 19 inches (483 mm).

The width of the absorbent pad 58 extending beyond the central region 35 should be at least as wide as the width of the absorbent pad 58 in the central region 35. The width of the absorbent pad 58 could be narrowed beyond the central region 35 but may compromise the leakage containment. In some cases, the width of the absorbent pad 58 is widened beyond the central region 35, especially where the garment 20 includes leg cutouts 900 in the central region 35. Because the absorbent pad 58 is disposed primarily in the front region 37, the central region 35, with less in the back region 39, a position shifted forward along the longitudinal axis of the garment 20, the leg cutouts 900 also would be shifted forward along the longitudinal axis of the garment 20 to accommodate the position of the garment 20 on the body of the wearer. The width of the absorbent pad 58 extending beyond the central region 35 is from about 2.5 inches (64 mm) to about 12 inches (305 mm), alternatively from about 4.0 inches (102 mm) to about 10 inches (254 mm). A preferred range is from about 5 inches (127 mm) to about 9 inches (229 mm).

The present invention contemplates various shapes of the absorbent pad 58. One preferred composite has a non-rectangular shape such as an hourglass or I-beamed shaped absorbent pad 58. Another preferred absorbent pad 58 embodiment is rectangular in shape with rounded ends. The essentially rectangular-shaped absorbent pad 58, i.e., an hourglass shape is more preferred since it can be squared off at the ends to provide a smoother appearance in the back of the garment 20 while providing a more comfortable body-contouring fit.

The absorbent pad 58 is positioned so as to be symmetrical about the central longitudinal axis A—A of the garment 20 and skewed forward along the central transverse axis B—B of the garment 20. In other words, the side edges 62 and 64 of the absorbent pad 58 are equidistant from side edges 48 and 50 of the aqueous-liquid-pervious body-side liner 40, respectively. The front end and back end edges 66 and 68, respectively, of the absorbent pad 58 are not equidistant from the front and back edges 44 and 46 of the aqueous-liquid-pervious body-side liner 40, respectively. The absorbent pad 58 is disposed primarily in the front region 37 and the central region 35. The front end edge 66 of the absorbent pad 58 is from about 5 inches (12.7 cm) to about 1 inch (2.5 cm), more preferably from about 4 inches (10.2 cm) to about 2.0 inch (5.1 cm), most preferably from about 4 inches (10.2 cm) to about 1.5 inches (3.8 cm) from the front edge 30 of the garment 20. The preferred distance is about 3 inches (7.6 cm). The back end edge 68 of the absorbent pad 58 is from 3 inches (7.6 cm) to about 7 inches (17.8 cm), more preferably from about 4 inches (10.2 cm) to about 7 inches (17.8 cm), most preferably from about 4.5 inches (11.4 cm) to about 7 inches (17.8 cm) from the back edge 32 of the garment 20.

Referring now to FIGS. 1, 9, 10, 11, and 12, in order to further understand what is meant by a skewed forward absorbent pad 58 along the central transverse axis it is necessary to define a "skew factor" of the absorbent pad 58 which in combination with the presence of an absorbent pad 58 in which more of the length of the absorbent pad 58 is in the front region 37 than in the back region 39 (the absorbent pad 58 is not placed symmetrically but is skewed forward in the garment 20) to define the invention. For the purposes of this invention "not placed symmetrically" means that more than about 20 mm or more of the absorbent pad 58 is in the front region 37 compared to the back region 39.

The skew factor is calculated using the following steps:
1. Divide the garment length into three equal regions, the front region 37, the central region 35, and the back region 39.
2. Determine what length of the absorbent pad 58 in the longitudinal or MD direction along line A—A of FIG. 2 is in each region (35, 37, and 39) of the garment 20.
3. Calculate the skew factor by dividing the length of the absorbent pad 58 in the back region 39 by the sum of the lengths of the absorbent pad 58 in the front region 37 and the central region 35.

Figure 9:
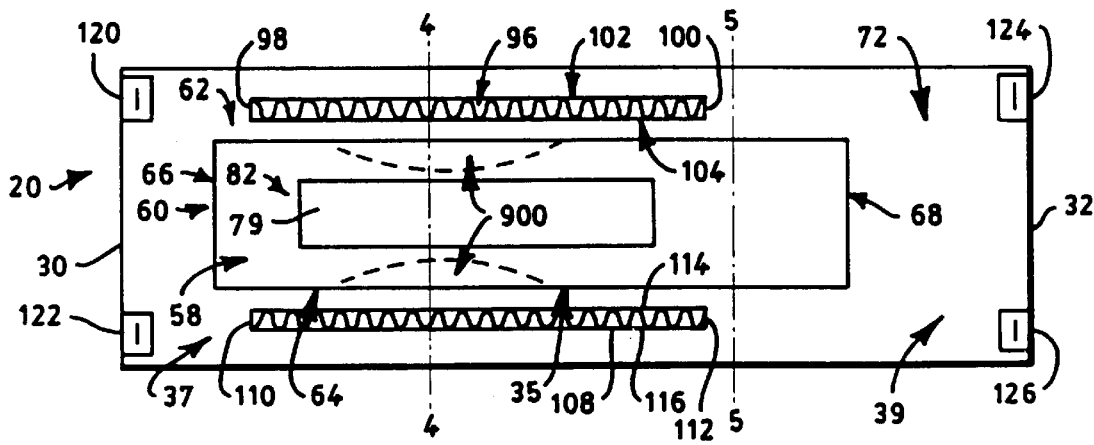
FIG. 9 is an expanded plan view of undergarment with a skewed forward placement of the absorbent pad in the MD direction.
Figure 10:
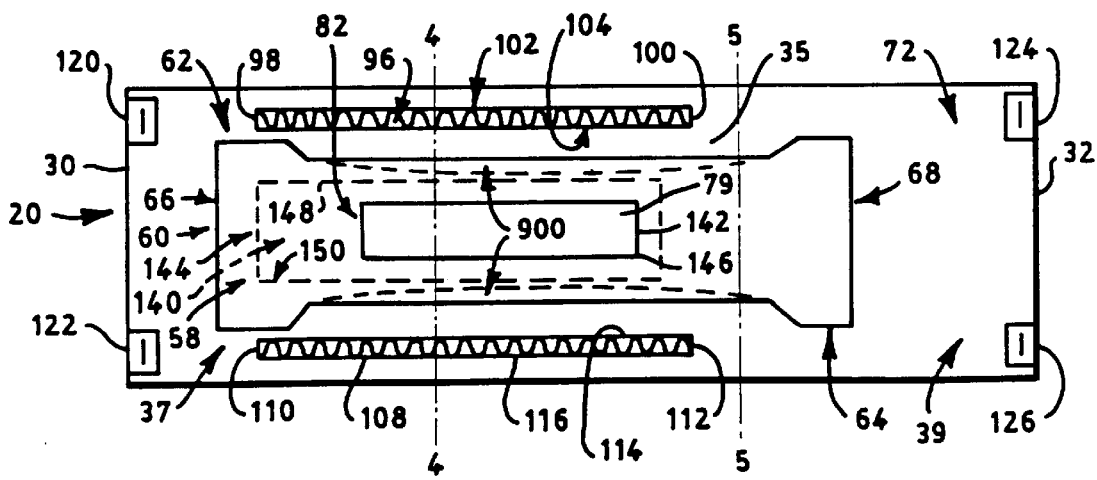
FIG. 10 is an expanded plan view of undergarment with a skewed forward placement of the absorbent pad and a high basis weight pocket in the MD direction.

Again referring to FIGS. 1, 9, 10, 11, and 12, because absorbent garments 20 such as undergarments, diapers, briefs, pants and the like have a large range of product lengths to fit people from infants through adults, the skew factor in conjunction with the presence of more or the absorbent pad 58 in the front region 37 than the back region 39 defines the amount of forward skew the absorbent pad 58 for any product length. The skew factor is a function of the overall length of the absorbent pad 58 and how it is placed in the disposable underpant 90, the undergarment 20, or other absorbent personal care product. Because the overall length of the disposable underpant 90 or the undergarment 20 affects how much of the pad is in the front region 37, the central region 35, and the back region 39, the skew factor is also a function of garment length. The placement of the absorbent pad 58 in any garment 20 depends on how that garment 20 is designed to fit on the wearer's body and the ability of the manufacturing process to control placement of the absorbent pad 58. For the purposes of this invention, the skew factor is a value less than about 0.10. Therefore, the range of skew factors disclosed in this invention for absorbent garments 20 with the absorbent pads 58 with a greater length in the front region 37 than in the back region 39 is above 0 to 0.10. For undergarment type incontinence garments 20, as shown in FIGS. 9 and 10, the range of skew factors is above 0 to 0.10 and more preferably from 0.7 to 0.10. For diapers (not shown), briefs (not shown), and the disposable underpant products (see FIGS. 11 and 12) the skew factor is preferably from above 0 to 0.10, more preferably from above 0 to 0.95, most preferably from 0.07 to 0.085.

In one embodiment of the invention referring to FIGS. 1, 2, 3a, 5, 6, and 9, the undergarment 20 has a length of 687 mm, a width of 218 mm and includes an absorbent pad 58 which has an MD length of 483 mm and a CD width of 114 mm. As shown in FIGS. 5 and 6, the absorbent pad 58 includes a homogeneous mixture of 210 gsm (grams per square meter) of DOW 2035 high absorbency material 202 (available from the DOW Chemical Company, Midland Mich.) and 391 gsm of Alliance CR1654 fluff pulp fibers 201. There is also a carded web intake material 79 in undergarment 20 which is 305 mm long and 76 mm wide with a basis weight of 85 gsm including a mixture of 40% by weight 6 denier polyester fibers from Hoechst Celanese and 60% 3 denier sheath core polyethylene/polypropylene crimped fibers from CHISSO Corporation of Japan. The intake material 79 is located between the body side liner 40 and the absorbent pad 58. The absorbent pad 58 has a retention capacity of about 500 grams of 0.9% sodium chloride in water.

Figure 8:
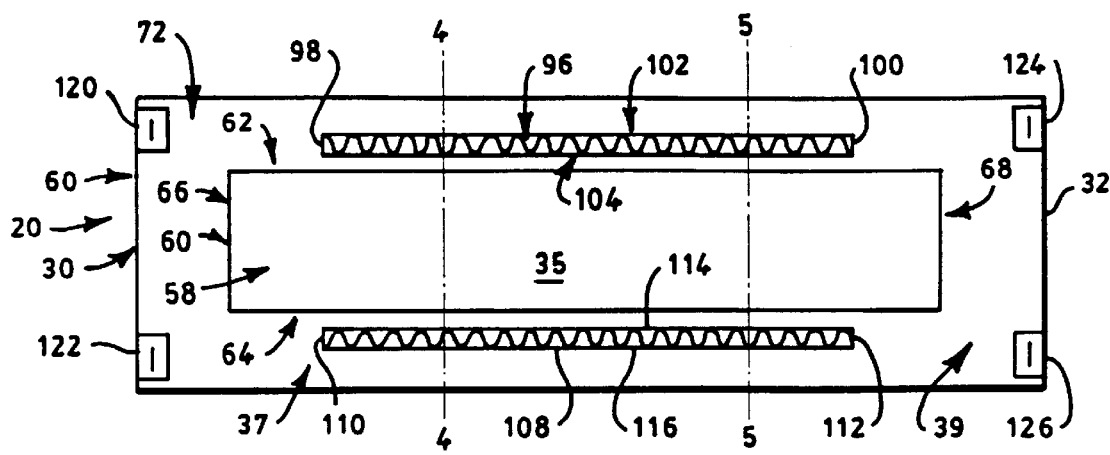
FIG. 8 is an expanded plan view of undergarment with a symmetrical placement of the absorbent pad.

The placement of the absorbent pad 58 is symmetric in the CD dimension of the undergarment 20 along the central longitudinal axis A—A in FIG. 2. Furthermore, the intake material 79 is placed so that its front end edge 82 is from the front end edge 30 of undergarment 20. None of the intake material 79 is located in the back region 39. When placed on the body of the wearer, this configuration results in a greater proportion of the absorbent pad 58 being on the anterior side of the wearer where it is more likely to be used. The undergarments 20 as shown in FIG. 8, have a symmetric placement of the absorbent pad 58 resulting in equal placement of the absorbent pad 58 in the anterior and posterior portions of the product resulting in lower utilization of the absorbent pad 58 and unsightly and uncomfortable bulk in the back region 39.

In another embodiment of the invention referring to FIGS. 1, 2, 3a, 5, 6, and 10, the undergarment 20 has a length of 687 mm, a width of 218 mm and includes an absorbent pad 58 which has an MD length of 423 mm and a CD width of 156 mm on the ends and 94 mm in the cutout region 900 along line 4—4. The cutout region 900 is 290 mm long and is symmetrically placed starting 70 mm from the front end edge 66 and the back end edge 68 of the absorbent pad 58. The cutout area 900 does not, however, have to be symmetrically placed from the front end edge 66 and the back end edge 68. In addition, the absorbent pad 58 has a pledget 140 placed between itself and the aqueous-liquid-impervious backing member 22 (FIGS. 1 and 4). The pledget 140 is 275 mm long and 89 mm wide. The front end edge 144 of pledget 140 is 146 mm from the front end edge 30 of the undergarment 20. Referring to FIGS. 5 and 6, the absorbent pad 58 includes a homogeneous mixture of 115 gsm (grams per square meter) of DOW 2035 high absorbency material 202 (available from the DOW Chemical Company, Midland Mich.) and 215 gsm of Alliance CR1654 fluff pulp fibers 201. There is also a carded web intake material 79 in the undergarment 20 which is 330 mm long and 76 mm wide with a basis weight of 85 gsm including a mixture of 40% by weight 6 denier polyester fibers from Hoechst Celanese and 60% 3 denier sheath core polyethylene/polypropylene crimped fibers from CHISSO Corporation of Japan. The intake material 79 is located between the body side liner 40 and the absorbent pad 58. Again referring to FIGS. 5 and 6, the pledget 140 includes a homogeneous mixture of 143 gsm (grams per square meter) of DOW 2035 high absorbency material 202 (available from the DOW Chemical Company, Midland Mich.) and 267 gsm of Alliance CR1654 fluff pulp fibers 201. The combined retention capacity of the absorbent pad 58 and the pledget 140 is about 500 grams of 0.9% sodium chloride in water. Importantly, the absorbent pad 58 is placed in the undergarment 20 so that the front end edge 66 of the absorbent pad 58 is 74 mm from the front end edge 30 of the undergarment 20. This results in 36.6% of the length of the absorbent pad 58 in the machine direction being placed in the front region 37 of the undergarment 20, 54.1% of the length of the absorbent pad 58 is in the central region 35 of undergarment 20 and only 9.3% of the length of the absorbent pad 58 is in the back region 39 of undergarment 20. The skew factor of the absorbent pad 58 is 0.102. The absorbent pad 58 and intake material 79 placement is symmetric in the CD dimension of the undergarment 20 along the central longitudinal axis 4—4 (see FIG. 2). Furthermore, the intake material 79 is placed so that its front end edge is 99 mm from the front end edge 30 of the undergarment 20. This results in 41.6% of the length of the intake material 79 being in the front region 37 and 58.4% of the length of the intake material 79 being in the central region 35. None of the length of the intake material 79 is located in the back region 39. When placed on the body of the wearer, this configuration results in a greater proportion of the absorbent pad 58 being on the anterior side of the wearer where it is more likely to be used. The undergarments 20 as shown in FIG. 8, have a symmetric placement of the absorbent pad 58 resulting in equal placement of the absorbent pad 58 in the anterior and posterior portions of the product resulting in lower utilization of the absorbent pad and unsightly and uncomfortable bulk in the back region 39.

Figure 11:
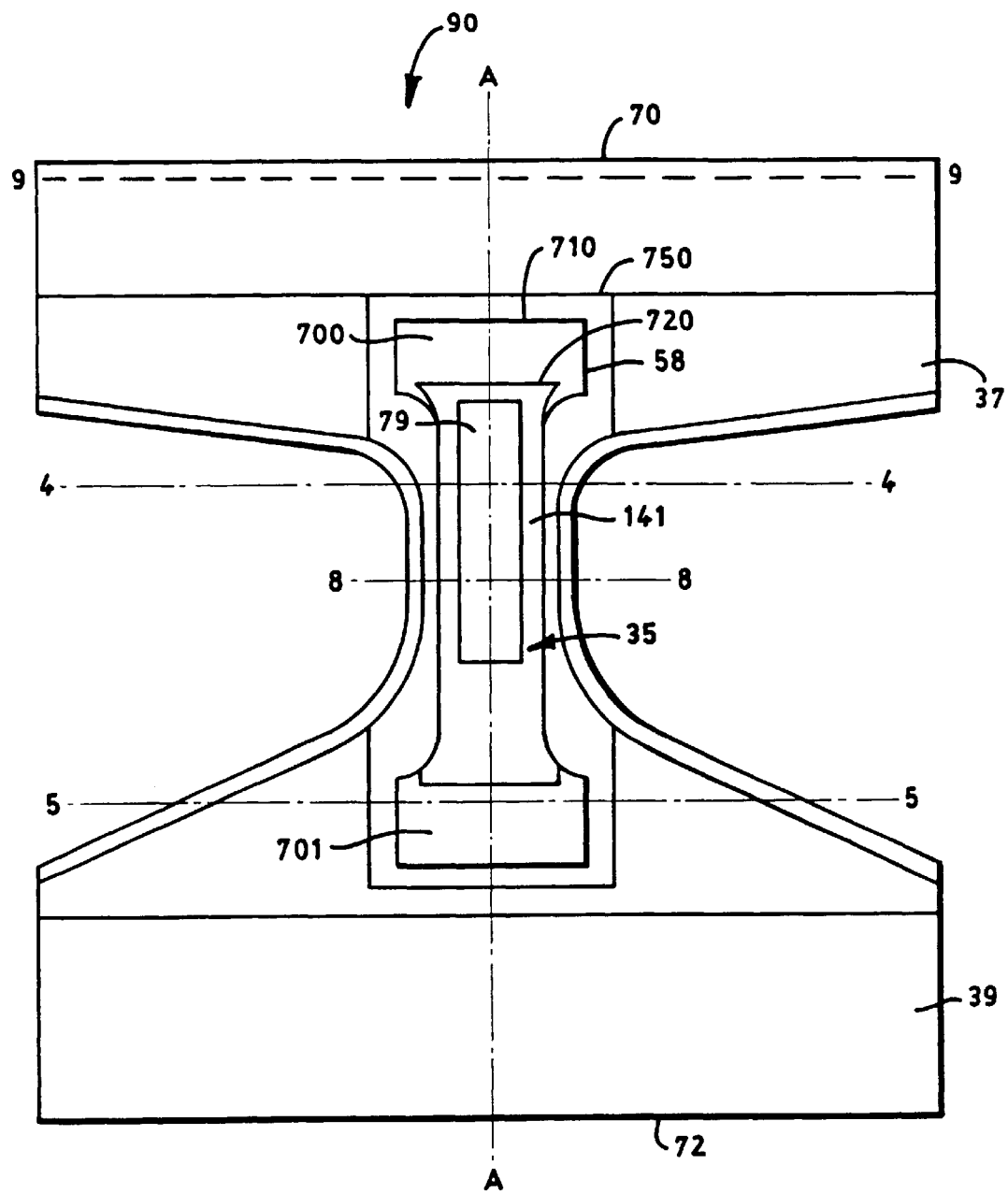
FIG. 11 is an expanded plan view of a pant with a skewed forward placement of the absorbent pad.

Referring to FIGS. 5, 6, and 11, in another embodiment a disposable underpant 90 has a length of 845 mm, a width of 715 mm at the ends along line 9—9 and a minimum width of 120 mm in the central region 35 along line 8—8 and includes an absorbent pad 58 which has an MD length of 438 mm and a CD width of 153 mm at the ends and of 89 mm in the center of the leg cut out 900 along line 8—8. The absorbent pad 58 is placed on aqueous-liquid-impervious backing member 750. The absorbent pad 58 also has a high basis weight pocket region 141 which has a length of 279 mm, a width of 89 mm along line 8—8 and a width of 102 mm at the ends. Referring to FIGS. 5 and 6, the absorbent pad 58 includes a homogeneous mixture of 129 gsm (grams per square meter) of DOW 2035 high absorbency material 202 (available from the DOW Chemical Company, Midland Mich.) and 215 gsm of Alliance CR1654 fluff pulp fibers 201 in the end regions 700 and 701. In the pocket region 140, the basis weight of high absorbency material 202 is 261 gsm and of fluff pulp fiber 201 is 435 gsm. There is also a carded web intake material 79 in the disposable underpant 90 which is 330 mm long and 76 mm wide with a basis weight of 85 gsm including a mixture of 40% by weight 6 denier polyester fibers from Hoechst Celanese and 60% 3 denier sheath core polyethylene/polypropylene crimped fibers from CHISSO Corporation of Japan. The intake material 79 is located between the body side liner 40 and the absorbent pad 58. The absorbent pad 58 has a retention capacity of about 500 grams of 0.9% sodium chloride in water. Importantly, the absorbent pad 58 is placed in the disposable underpant 90 so that the front end edge 710 of the absorbent pad 58 is 163 mm from the front end edge 710 of the disposable underpant 90. Furthermore, the front end edge 720 of the pocket region 141 is placed 222 mm from the front end edge 710 of the disposable underpant 90. Finally, an 85 gsm surge material (intake material) 79 with a length dimension of 279 mm and a width of 64 mm is placed coextensive with the pocket region in the length dimension and centered in the width dimension is placed on the body side of absorbent pad 58. The absorbent pad 58 has a retention capacity of about 500 grams of 0.9% sodium chloride in water. This results in 27.1% of the length of absorbent pad 58 in the machine direction being placed in the front region 37 of the disposable underpant 90, 64.2% of the length of the absorbent pad 58 being in the central region 35 of the disposable underpant 90 and 8.7% of the length of the absorbent pad 58 being in the back region 39 of the disposable underpant 90. The absorbent pad 58 has a skew factor of 0.095. Additionally, 21.5% of the length of the pocket region 141 is in the front region 37, 78.5% of the length of the pocket region 141 is in the central region 35 and 0.0% of the length of the pocket region 141 is in the back region 39. The absorbent pad 58 and intake material 79 placement is symmetric in the CD dimension of the disposable underpant 90 along the central longitudinal axis A—A in FIG. 12. When placed on the body of the wearer, this configuration results in a greater proportion of the absorbent pad being on the anterior side of the wearer where it is more likely to be used. Compared to symmetric placement of the absorbent pad 58 in the MD length of the disposable underpant resulting in equal placement of the absorbent pad 58 in the anterior and posterior portions of the product, the skewed forward configuration described above results in higher utilization of the absorbent pad 58 and prevents unsightly and uncomfortable bulk in the back region 39 of the disposable underpant 90.

Figure 12:
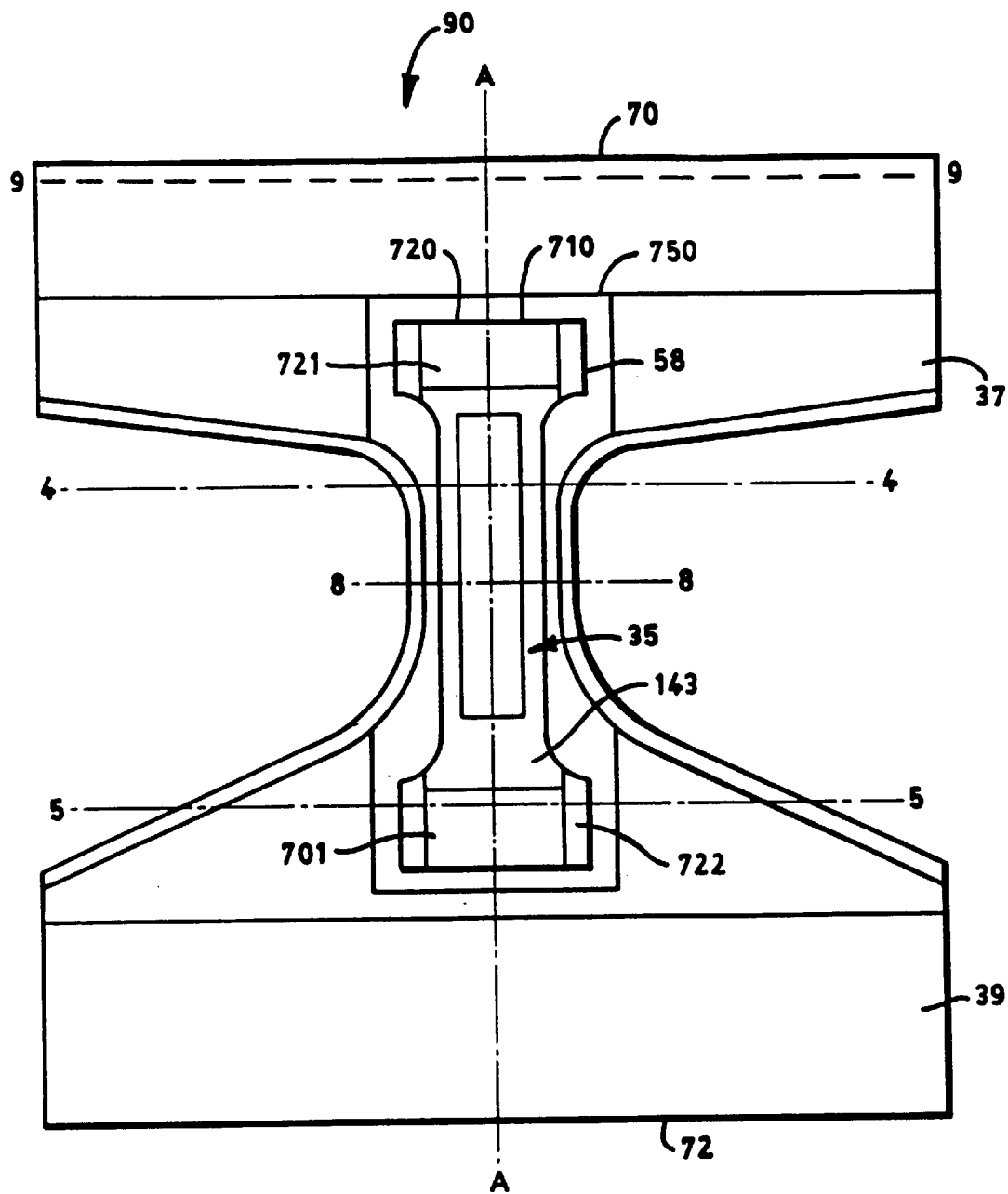
FIG. 12 is an expanded plan view of a pant with a skewed forward placement of a profile absorbent pad.

Referring to FIGS. 5, 6, and 12 in yet another embodiment, a disposable underpant 90 has a length of 845 mm, a width of 715 mm at the ends along line 9—9 and a minimum width of 120 mm in the central region along line 8—8 and includes an absorbent pad 58 which has an MD length of 489 mm and a CD width of 153 mm at the ends and of 89 mm in the center of the leg cutout 900 along line 8—8. The absorbent pad 58 is placed on the aqueous-liquid-impervious backing member 750. The absorbent pad 58 also has a high basis weight pocket region 143 which has a length of 489 mm (full length of the absorbent pad 58), a width of 89 mm along line 8—8 and a width of 102 mm at the ends.

Referring to FIGS. 5a and 6, the absorbent pad 58 includes a homogeneous mixture of 114 gsm (grams per square meter) of DOW 2035 high absorbency material 202 (available from the DOW Chemical Company, Midland Mich.) and 232 gsm of Alliance CR1654 fluff pulp fibers 201 in the side end regions 721 and 722. In the pocket region 143, the basis weight of high absorbency material is 282 gsm and of fluff pulp 591 gsm. The absorbent pad 58 has a retention capacity of about 800 grams of 0.9% sodium chloride in water. Importantly, the absorbent pad 58 is placed in the disposable underpant 90 so that the front end edge 710 of the absorbent pad 58 is 112 mm from the front end edge 710 of the disposable underpant 90. Finally, an 85 gsm surge material (intake material) 79 with a length dimension of 279 mm and a width of 64 mm is placed 187 mm from the front end edge 710 of the disposable underpant 90 and is centered in the width dimension along the central longitudinal axis A—A is placed on the body side of the absorbent pad 58. This results in 34.7% of the length of the absorbent pad 58 in the machine direction being placed in the front region 37 of the disposable underpant 90, 57.6% of the length of the absorbent pad 58 is in the central region 35 of the disposable underpant 90 and 7.7% of the length of the absorbent pad 58 is in the back region 39 of the disposable underpant 90. The absorbent pad 58 has a skew factor of 0.082. The absorbent pad 58 and intake material 79 placement is symmetric in the CD dimension of the disposable underpant 90 along the central longitudinal axis A—A. When placed on the body of the wearer, this configuration results in a greater proportion of the absorbent pad 58 being on the anterior side of the wearer where it is more likely to be used. Compared to symmetric placement of the absorbent pad 58 in the MD length of the disposable underpant 90 resulting in equal placement of the absorbent pad 58 in the anterior and posterior portions of the product, the skewed forward configuration described above results in higher utilization of the absorbent pad 58 and prevents unsightly and uncomfortable bulk in the back region 39 of the disposable underpant 90.

A leg elastic 96 has a front edge 98, a back edge 100, an exterior side edge 102 and an interior side edge 104. The leg elastic 96 is affixed adjacent the side edge 48 of the aqueous-liquid-pervious body-side liner 40 so as to be spaced inwardly therefrom. The leg elastic 96 is positioned so that the front edge 98 and the back edge 100 are equidistant from their respective front and back edges 44 and 46 of the aqueous-liquid-pervious body-side liner 40. However, the leg elastic 96 can be positioned other than in an equidistant arrangement relative to their front and back edges 98 and 100 and the front and back edges 44 and 46 of the aqueous-liquid-pervious body-side liner 40. The leg elastic 96 can be positioned such that the front and back edge 98 and 100 are equidistant from the front end and back end edges 66 and 68 of the absorbent pad 58. Additionally, the leg elastic 96 can be positioned such that the front and back edges 98 and 100 are not equidistant from the front end and back end edges 66 and 68 of the absorbent pad 58.

A second leg elastic 108 has a front edge 110, a back edge 112, an interior side edge 114, and an exterior side edge 116. The leg elastic 108 is affixed to the aqueous-liquid-pervious body-side liner 40 so as to be adjacent to the side edge 50, and is spaced inwardly of the side edge 50. The leg elastic 108 is positioned so that its front edge 110 and back edge 112 are spaced equidistant from their respective front and back edges 44 and 46 of the aqueous-liquid-pervious body-side liner 40. The leg elastic 108 can also be positioned other than in an equidistant arrangement. The leg elastic 108 can be positioned such that the front and back edges 110 and 112 are equidistant from the front end and back end edges 66 and 68 of the absorbent pad 58. Additionally, the leg elastic 96 can be positioned such that the front and back edges 98 and 100 are not equidistant from the front end and the back end edges 66 and 68 of the absorbent pad 58.

While the leg elastics 96 and 108 closely follow the edge of the absorbent pad 58 outside of the central region 35, moving the leg elastics 96 and 108 away from the absorbent pad 58, the absorbent pad 58 interferes less with the function of the leg elastics 96 and 108, providing better gasketing around the legs of the wearer. In addition, as the absorbent pad 58 swells as it absorbs bodily discharges, the leg elastics 96 and 108 so positioned are better able to remain in contact with and conform to the wearer's body. Such a placement of the leg elastics 96 and 108 is especially beneficial in garments 20 having leg cutouts 900, as fit, protection, and comfort of the garments 20 are preferred.

In a preferred embodiment, leg elastics 96 and 108 are attached to the garment 20 sandwiched between the backing member 22 and the body-side liner 40, in a stretched state by ultrasonic bonded, heat/pressure bonded or adhesively bonded. The leg elastics 96 and 108 are attached in a stretched state by ultrasonic bonded, heat/pressure bonded or adhesively bonded. Materials suitable for the elastics include elastic strands, yarn rubber, flat rubber, elastic tape, film-type rubber, polyurethane and elastomeric, tape-like elastomeric or foam polyurethane or formed elastic or non-elastic scrim. Suitable material is sold under the name LYCRA® by the DuPont Company located in Wilmington, Del. Each elastic is unitary, multi-part or composite in construction before integrating into the garment 20.

In an alternative embodiment, leg elastics 96 and 108 are attached to the garment 20 sandwiched between the outer member 38 and the backing member 22 in a stretched state by ultrasonic bonded, heat/pressure bonded, or adhesively bonded.

The leg elastics 96 and 108 are from about 0.0625 inch (1.6 mm) to about 1 inch (25 mm) wide, more preferably from about 0.25 inch (6 mm) to about 1 inch (25 mm), and most preferably from about 0.25 inch (6 mm) to about 0.75 inch (18 mm) such as 0.5 inch (13 mm). The leg elastics 96 and 108 are applied under an elongation of from about 100% to about 350%, more preferably under an elongation of from about 150% to about 275%, and most preferably under an elongation of from about 225% to about 275%.

The leg elastics 96 and 108 include threads, strands, ribbons, bands, film, elastic nonwovens, or composite. The threads, strands, ribbons, or bands are multiple and are applied as a composite. The number of pieces of elastic material including the leg elastic 96 and 108 ranges from about 1 to about 6, preferably from about 2 to about 5, and more preferably from about 3 to about 4. Preferably, when the leg elastics 96 and 108 are threads, 1 to 6 threads are used as the leg elastics 96 and 108, and the threads are spaced from about 0.0625 inch (1.6 mm) to about 0.5 inches (13 mm), preferably from about 0.0625 inch (1.6 mm) to about 0.25 inch (6 mm), and more preferably about 0.125 inch (3 mm) apart.

The threads are made of an elastomeric material. One material is spandex such as LYCRA® threads available from DuPont located in Wilmington, Del. Suitable leg elastics 96 and 108 include threads having a decitex (g/10000 m) of from about 470 to about 1200, preferably from about 620 to about 1000, and more preferably from about 740 to about 940 for leg elastics 96 and 108 including from about 3 to about 6 threads. Adhesive 118, (FIG. 3) preferably applied in a meltblown or swirl pattern is used to bond the leg elastics 96 and 108 to the outer member 38, the body-side liner 40, or the backing member 22. Preferably, the adhesive 118 is applied only to the leg elastics 96 and 108. A suitable adhesive includes, for example, Findley H2096 hot melt adhesive available from Ato Findley Adhesives located in Milwaukee, Wis.

In one embodiment, to provide a snug fit around the legs of the wearer and to draw up the sides of the central region 35 to form a cradle structure around the absorbent pad 58, the leg elastics 96 and 108 are applied to the backing member 22 or the body-side liner 40 under an elongation of about 225% to about 275%. The leg elastics 96 and 108 are sandwiched between the backing member 22 and the body-side liner 40 under an elongation more preferably of about 200%.

In another embodiment, providing a snug fit around the legs of the wearer and drawing the sides of the central region 35 up to form a cradle structure around the absorbent pad 58, the leg elastics 96 and 108 are applied to the outer member 38 or the backing member 22 under an elongation of about 200% to about 250%. The leg elastics 96 and 108 are sandwiched between the outer member 38 and the backing member 22 under an elongation preferably of about 200%.

In one embodiment, it is preferred to center the leg elastics 96 and 108 between the front end edge 66 and the back end edge 68 of the absorbent pad 58.

In one embodiment, the leg elastics 96 and 108 are made of urethane. Leg elastics 96 and 108 can be made of natural rubber or other synthetic elastic material.

When stretched for adherence to the garment 20, the leg elastics 96 and 108 have a length of about 14 inches (35.6 cm) and a width of about 0.42 inches (1.06 cm). When the leg elastics 96 and 108 relax, they each are of a length equal to about 16.5 cm and a width of about 1.27 cm.

A pair of slits 120 and 122, such as button holes, are contained in the container 74 including the aqueous-liquid-pervious body-side liner 40 and the aqueous-liquid-impervious backing member 22 adjacent the front edge 30 of the garment 20. Another pair of slits 124 and 126, such as button holes, are contained in the container 74 including the aqueous-liquid-pervious body-side liner 40 and aqueous-liquid-impervious backing member 22 adjacent the back edge 32 of the garment 20. A strap 130 having retainers 132 and 134, such as buttons, each at opposite ends, extends between the slits 120 and 124. Another strap 136 having retainers 138 and 139, such as buttons, each at opposite ends, extends between the slits 122 and 126. This support system is described in U.S. Pat. No. 4,315,508 issued Feb. 16, 1982 to Bolick, which is incorporated herein by reference.

Other means for securing the garment around the individual includes mechanical type fasteners. The mechanical type fasteners include snaps, buckles, clasps, hooks and loops, end extensions, tabs, and adhesive tapes, to interlock or engage the outer cover of the garment. Elasticized fasteners are used in assuring better fit of such garments. Absorbent garments 20 include fully encircling or pre-fastened waist bands.

The leg elastics 96 and 108 effectively seal between the body of the wearer and the garment 20 so as to provide good containment properties in the central region 35.

EXAMPLE 1

Ten incontinent panelists were recruited to determine what portions of an undergarment were actually wetted in use. Each panelist was given commercially available DEPEND® undergarments available from Kimberly-Clark Corporation of Dallas, Tex. The DEPEND® undergarment had a full product length of 686 mm and the absorbent pad was 534 mm long and place symmetrically in the undergarment with the front and back end edges of the absorbent pad being 76 mm from the respective front and back end edges of the undergarment. Each product was marked on the front side so the researchers would know which end was placed on the anterior portion of the body. Each panelist was instructed to wear the undergarment as they normally do, but rather than rolling them up as they normally do and discarding them, they would "box" the used product. Each box unit consisted of three major pieces: a flat piece of cardboard approximately the size of an undergarment with a peel strip down the center, a plastic bag, and an outside box. The panelists were instructed to remove the peel strip and carefully place the used undergarment on it, being careful not to stretch out the undergarment but to let it reside naturally. Then they would slide the cardboard and product into the plastic bag and box. Each product had a matching diary sheet so leakage information about that particular product was known while it was being examined. Each panelist was given four products to wear during a 24 hour period.

Each used product was measured to determine what area of the product fit between the users legs and what the distance of the typical insult was from the front and back end edges of the absorbent pad. The results appear in the Table 1.

TABLE 1

Insult Distance Analysis
Distance from Front End Edge of Undergarment

| Longitudinal Distance Range Between Users Legs (From Front End Edge of Undergarment Product) | Average Distance of Insult Wetness from Front End Edge of Absorbent Pad | Average Distance of Insult Wetness from Back End Edge of Absorbent Pad |
|---|---|---|
| 198 to 256 mm | 58 mm | 211 mm |

Comparison of the data in the table to the description of the undergarment product dimensions clearly shows that the input of urine into the products is highly skewed to the front of the garment. The center point of the product is 343 mm for full product length and 267 mm for the absorbent pad. Because all of the numbers in TABLE 1 are much less than 343, it suggests that a more efficient and better performing product should have the absorbent pad concentrated more to the front.

EXAMPLE 2

Undergarments were sent to 87 incontinent panelists (65 females, 22 males) who used them under normal use conditions. A diary sheet, with pre-written questions, was provided for all individual products on which panelists recorded information pertaining to leakage. All used products were returned and weighed to determine the amount of urine they contained. From the combined data, a step procedure for logistic regression was used to determine the best fitting model for the leakage data. The goal of logistic regression is to describe the relationship between leaks and the set of explanatory variables (codes, urine grams, gender, activity, and panelist hip size).

The undergarment products tested had overall dimensions of about 8.7 inches (22.1 cm) wide and 27 inches (68.6 cm) long and a design as generally shown in FIG. 1 and FIG. 9. The absorbent pads were all 19" in length. The pads had a ratio of 35% superabsorbent to 65% fluff fibers throughout the entire length with a target density of 0.160 g/cm$^3$. In addition, all products had about a 3 inch (7.6 cm) wide by 12 inch (30.5 cm) long intake layer with a basis weight of 85 gsm.

Products A and B had 4.5 inches (11.4 cm) wide absorbent pads and differed in the location of the absorbent pad in relation to the front of the undergarment and in the location of the intake layer in relation to the front of the absorbent pad as shown in TABLE 2.

Products C and D had I-shaped absorbent pads with the absorbent pad being 4.5 inches (11.4 cm) at its widest part and 3.5 inches (8.9 cm) at its narrowest point. The length of the narrowed (3.5 inch) portion of the pad had a MD length of 10 inches (25.4 cm). The products differed in the location of the absorbent pad in relation to the front of the undergarment, in the location of the intake layer in relation to the front of the absorbent pad, and in the location of the 10 inch (25.4 cm) long, 3.5 inches (8.9 cm) wide, the narrowed portion of the absorbent pad, in relation to the front of the absorbent pad. As shown in TABLE 2.

TABLE 2

| Absorbent Pad Length (inches) | Distance A | Distance B | Distance C |
| --- | --- | --- | --- |
| A 19 | 4 | 3.5 | N/A |
| B 19 | 3 | 1 | N/A |
| C 19 | 4 | 3.5 | 4.5 |
| D 19 | 3 | 1 | 3 |

Distance A.
Distance from front of absorbent pad to front of undergarment (inches)
Distance B.
Distance from front of intake layer to front of absorbent pad (inches)
Distance C.
Distance from front of 3.5 inch wide narrowed portion of absorbent pad to front of absorbent pad (inches)

Referring to FIG. 9, TABLE 3 uses the data in TABLE 2 to calculate the percentages of the absorbent pad 58 and the intake material 79 in the front region 37, the central region 35, and the back region 39 of the undergarment 20. The data clearly shows that codes B and D have absorbent pads 58 and intake material 79 which are much more skewed to the front of the undergarment 20 than codes A and C.

TABLE 3

Pad and Intake Layer Percentages
Front Region, Central Region, and Back Region

| Code | Skew Factor | Absorbent Pad % In | | | Intake Layer % In | | |
| --- | --- | --- | --- | --- | --- | --- | --- |
| | | Front | Central | Back | Front | Central | Back |
| A | Not Skewed | 26.3 | 47.4 | 26.3 | 10.2 | 75.1 | 14.7 |
| B | 0.264 | 31.7 | 47.4 | 20.9 | 42.0 | 58.0 | 0.0 |
| C | Not Skewed | 26.3 | 47.4 | 26.3 | 10.2 | 75.1 | 14.7 |
| D | 0.264 | 31.7 | 47.4 | 20.9 | 42.0 | 58.0 | 0.0 |

The leakage probability data in TABLE 4 shows the improvements seen in leakage performance when the absorbent components, absorbent pad and intake layer, and shape are skewed forward towards the front of the undergarment. Codes B and D have the lowest leakage probabilities and Code D which also includes a highly skewed forward leg cutout region has the lowest leakage probabilities of all.

TABLE 4

Leakage Probabilities at Various Urine Loadings (grams)

| | 25 g | 125 g | 350 g |
| --- | --- | --- | --- |
| A | 0.076 | 0.142 | 0.440 |
| B | 0.051 | 0.106 | 0.414 |
| C | 0.051 | 0.109 | 0.440 |
| D | 0.041 | 0.095 | 0.436 |

Note:
Leakage probability is the chance that a product will leak when subjected to a given loading of urine during use. A 100% chance of leaking has a probability of 1.00.

EXAMPLE 3

Two absorbent pant products were tested for leakage protection performance. Pants were sent to 72 incontinent panelists (44 females, 28 males) who used them under normal use conditions. A diary sheet, with pre-written questions, was provided for all individual products on which panelists recorded information pertaining to leakage. All used products were returned and weighed to determine the amount of urine they contained. From the combined data, a step procedure for logistic regression was used to determine the best fitting model for the leakage data. The goal of logistic regression is to describe the relationship between leaks and the set of explanatory variables (codes, urine grams, gender, activity, and panelist hip size).

The products tested were a prototype pant and the Sure-Care® Slip-On Undergarment produced by Inbrand Corporation of Marietta, Ga. The Slip-on product is a traditional pant with a symmetrical placement of the absorbent material in the product chassis while the prototype had a highly skewed forward absorbent pad with less capacity than the SureCare product. The SureCare product is 660 mm long and has an essentially rectangular absorbent pad which is 550 mm long and 127 mm wide. The absorbent pad has 90 gsm of high absorbency material and 1062 gsm of fluff pulp. The pad is placed 55 mm from the front and back end edges of the garment.

The prototype pant 90 (referring to FIG. 11) has a product length of 781 mm. The absorbent pad is 400 mm long and 165 mm wide at the ends and 90 mm wide in the center. The pad is placed 160 mm from the front end edge of the pant and 221 mm from the back end edge of the pant. The pad includes 110 gsm of high absorbency material and 165 gsm of fluff fibers. In addition, the prototype has a pledget which is 292 mm long, 90 mm wide and placed 185 mm from the front end edge of the pant and 304 mm from the back end edge of the pant between the absorbent pad and the backing member. The pledget is comprised of 180 gsm of high absorbency material and 270 gsm of fluff fibers. The density of the pad and pledget is about 0.160 gm/cc. In addition, the prototype has a 100 gsm intake material which is 64 mm wide and 203 mm long. The front end edge of the intake material is 216 mm from the front end edge of the pant prototype and 362 mm from the back end edge of the pant. The proportions of the absorbent pads and pledgets in the front region, central region, and back region are shown in Table 5. Table 5 shows that the absorbent pad, pledget, and intake material of the prototype are skewed to the front of the product with higher proportions of the absorbent in the front while the SureCare product has symmetric placement of its absorbent pad.

TABLE 5

Dimensional Comparison of Prototype and SureCare Slip-On

| Product | Absorbent Component | % in Front Region | % in Central Region | % in Back Region | Retention Capacity 0.9% Saline |
| --- | --- | --- | --- | --- | --- |
| Sure-Care | Absorbent Pad | 30.0 | 40.0 | 30.0 | 726 g |
| Prototype | Absorbent Pad | 25.0 | 65.0 | 9.8 | 480 g |
| | Pledget | 25.7 | 74.3 | 0.0 | |
| | Intake Layer | 21.2 | 78.8 | 0.0 | |

The SureCare product in TABLE 5 does not have a skew factor because it is symmetric. On the other hand, the skew factor of the prototype absorbent pad is 0.111 showing it to be highly skewed forward.

The leakage information in TABLE 6, expressed as the urine load in grams at which 20% (LD20) and 50% (LD50)

of the products leak clearly shows that the pant prototype with the skewed forward absorbent provides better leakage protection because a higher urine load is needed to make 20% and 50% of the products leak.

TABLE 6

Leakage Protection of SureCare Slip-on versus Prototype Pant

| Product | Gender | LD20, grams | LD50, grams |
|---------|--------|-------------|-------------|
| SureCare | Male | 240 | 367 |
|  | Female | 84 | 231 |
| Prototype | Male | 294 | 450 |
|  | Female | 294 | 441 |

While various and other reference materials have been incorporated herein by reference, to the extent there is any inconsistency between incorporated material and that of the written specification, the written specification shall control. In addition, while the invention has been described in detail with respect to specific embodiments thereof, it will be apparent to those skilled in the art that various alterations, modifications and other changes may be made to the invention without departing from the spirit and scope of the present invention. It is therefore intended that the claims cover all such modifications, alterations and other changes encompassed by the appended claims.

What is claimed is:

1. A disposable absorbent garment having an initial expanded shape, a longitudinal axis and a transverse axis, a front region, and a back region, said front region and said back region being oppositely positioned on said longitudinal axis, and a central region positioned between said front region and said back region, wherein said front region, said back region, and said central region each have a length along said longitudinal axis of one third of the length of said absorbent garment, comprising:

an aqueous liquid-impervious backing member;
an aqueous liquid pervious body-side liner joined to said backing member to form a joined body-side liner and backing member connected along a periphery of said joined body-side liner and backing member;
a rectangular absorbent pad, having a front end edge and a back end edge, positioned between said bodyside liner and said backing member inboard of said periphery of said joined liner and said backing member; and
elastic gathers aligned along longitudinally extending margins of said periphery, rendering said garment elastically contractible and body-conforming adjacent the crotch of the wearer,
wherein said absorbent pad is positioned within said regions such that the length of said absorbent pad in the back region divided by the length of said absorbent pad in said front region and said central region is less than 0.10 and said length of said absorbent pad in said front region is greater than said length of absorbent pad in said back region.

2. The disposable absorbent garment according to claim 1, wherein said absorbent garment further comprises a front waist region, a back waist region, said front waist region and said back waist region being oppositely positioned on said longitudinal axis and a crotch region positioned between said front waist region and said back waist region.

3. The disposable absorbent garment according to claim 2, wherein said front waist region further comprises a front edge, and said back waist region further comprises a back edge.

4. The disposable absorbent garment according to claim 3, wherein said front end edge of said absorbent pad is positioned from about 7 inches to about 3 inches from said front edge of said front waist region and said back end edge of said absorbent pad is positioned from about 4 inches to about 10 inches from said back edge of said back waist region.

5. The disposable absorbent garment according to claim 4, wherein said absorbent pad is positioned symmetrically relative to said longitudinal axis.

6. The disposable absorbent garment according to claim 1, wherein the length of said absorbent pad is from about 15 inches to about 21 inches.

7. The disposable absorbent garment according to claim 2, wherein the length of said absorbent pad is from about 15 inches to about 21 inches.

8. The disposable absorbent garment according to claim 1, wherein the length of said absorbent pad is from about 55 percent to about 80 percent of the length of said backing member.

9. The disposable absorbent garment according to claim 1, wherein said garment has a rectangular shape.

10. The disposable absorbent garment according to claim 1, wherein said garment has a rectangular shape with leg cutouts.

11. The disposable absorbent garment according to claim 1, wherein said garment further comprises a surge layer positioned between said absorbent pad and said body-side liner.

12. The disposable absorbent garment according to claim 1, wherein said garment further comprises a surge layer positioned between said absorbent pad and said body-side liner, said surge layer being positioned symmetrically relative to the longitudinal axis of the expanded garment and sized to have a length and width less than the length and width of said absorbent pad.

13. The disposable, absorbent garment according to claim 1, wherein said absorbent pad has a rectangular shape.

14. A method of providing a disposable absorbent garment, comprising:

a) Providing an initial expanded shape having a longitudinal axis, a transverse axis, a front region, and a back region;
b) Positioning said front region and said back region oppositely on said longitudinal axis;
c) Positioning a central region between said front region and said back region, wherein said front region, said back region, and said central region each have a length along said longitudinal axis of one third of the length of said absorbent garment;
d) Providing an aqueous-liquid-impervious backing member;
e) Joining an aqueous-liquid-pervious body-side liner to said backing member to form a joined body-side liner and backing member connected along a periphery of said joined body-side liner and backing member;
f) Positioning a rectangular absorbent pad, having a front end edge and a back end edge, between said bodyside liner and said backing member inboard of said periphery of said joined liner and said backing member;
g) Providing elastic gathers aligned along longitudinally extending margins of said periphery, rendering said garment elastically contractible and body-conforming adjacent the crotch of the wearer; and
h) Positioning said absorbent pad within said regions such that the length of said absorbent pad in the back region divided by the length of said absorbent pad in said front region and said central region is less than 0.10 and said length of said absorbent pad in said front region is greater than said length of absorbent pad in said back region.

15. A method of providing a disposable absorbent garment as set forth in claim 14, further comprising positioning a front waist region on said absorbent garment opposite a back waist region on said longitudinal axis, and positioning a crotch region between said front waist region and said back waist region.

16. A method of providing a disposable absorbent garment as set forth in claim 15, wherein said front waist region further comprises a front edge, and said back waist region further comprises a back edge.

17. A method of providing a disposable absorbent garment as set forth in claim 16, further comprising positioning said front end edge of said absorbent pad from about 7 inches to about 3 inches from said front edge of said front waist region and positioning said back end edge of said absorbent pad from about 4 inches to about 10 inches from said back edge of said back waist region.

18. A method of providing a disposable absorbent garment as set forth in claim 17, further comprising positioning said absorbent pad symmetrically relative to said longitudinal axis.

19. A method of providing a disposable absorbent garment as set forth in claim 14, wherein the length of said absorbent pad is from about 15 inches to about 21 inches.

20. A method of providing a disposable absorbent garment as set forth in claim 14, wherein the length of said absorbent pad is from about 15 inches to about 21 inches.

21. A method of providing a disposable absorbent garment as set forth in claim 14, wherein the length of said absorbent pad is from about 55 percent to about 80 percent of the length of said backing member.

22. A method of providing a disposable absorbent garment as set forth in claim 14, wherein said garment has a rectangular shape.

23. A method of providing a disposable absorbent garment as set forth in claim 14, wherein said garment has a rectangular shape with leg cutouts.

24. A method of providing a disposable absorbent garment as set forth in claim 14, further comprising positioning a surge layer between said absorbent pad and said body-side liner.

25. A method of providing a disposable absorbent garment as set forth in claim 14, further comprising symmetrically positioning a surge layer between said absorbent pad and said body-side liner relative to the longitudinal axis of the expanded garment and sizing said surge layer have a length and width less than the length and width of said absorbent pad.

26. A method of providing a disposable absorbent garment as set forth in claim 14, wherein said absorbent pad has a rectangular shape.

27. A disposable absorbent garment, comprising:

an initial expanded shape having a longitudinal axis, a transverse axis, a front region, and a back region, said front region and said back region being oppositely positioned on said longitudinal axis, and a central region positioned between said front region and said back region, wherein said front region, said back region, and said central region each have a length along said longitudinal axis of one third of the length of said absorbent garment;

a front waist region having a front edge, a back waist region having a back edge, said front waist region and said back waist region being oppositely positioned on said longitudinal axis and a crotch region positioned between said front waist region and said back waist region;

an aqueous-liquid-impervious backing member;

an aqueous-liquid-pervious body-side liner joined to said backing member to form a joined body-side liner and backing member connected along a periphery of said joined body-side liner and backing member;

a rectangular absorbent pad, having a front end edge and a back end edge, positioned symmetrically relative to said longitudinal axis between said bodyside liner and said backing member inboard of said periphery of said joined liner and said backing member; and elastic gathers aligned along longitudinally extending margins of said periphery, rendering said garment elastically contractible and body-conforming adjacent the crotch of the wearer;

wherein said absorbent pad is positioned within said regions such that the length of said absorbent pad in the back region divided by the length of said absorbent pad in said front region and said central region is less than 0.10 and said length of said absorbent pad in said front region is greater than said length of absorbent pad in said back region;

wherein said front end edge of said absorbent pad is positioned from about 7 inches to about 3 inches from said front edge of said front waist region and said back end edge of said absorbent pad is positioned from about 4 inches to about 10 inches from said back edge of said back waist region;

wherein the length of said absorbent pad is from about 15 inches to about 21 inches and from about 55 percent to about 80 percent of the length of said backing member; and wherein said garment has a rectangular shape with leg cutouts and a surge layer between said absorbent pad and said body-side liner symmetrically positioned relative to said longitudinal axis of the expanded garment and sized to have a length and width less than the length and width of said absorbent pad.

* * * * *